(12) United States Patent
Burton et al.

(10) Patent No.: US 9,315,388 B2
(45) Date of Patent: Apr. 19, 2016

(54) PRODUCTION OF GRAPHENE MATERIALS IN A CAVITATING FLUID

(71) Applicants: David Joseph Burton, Waynesville, OH (US); Bor Z Jang, Centerville, OH (US); Aruna Zhamu, Centerville, OH (US)

(72) Inventors: David Joseph Burton, Waynesville, OH (US); Bor Z Jang, Centerville, OH (US); Aruna Zhamu, Centerville, OH (US)

(73) Assignee: Nanotek Instruments, Inc.

( * ) Notice: Subject to any disclaimer, the term of this patent is extended or adjusted under 35 U.S.C. 154(b) by 32 days.

(21) Appl. No.: 13/999,397

(22) Filed: Feb. 21, 2014

(65) Prior Publication Data
US 2015/0239741 A1 Aug. 27, 2015

(51) Int. Cl.
| | |
|---|---|
| *C01B 31/04* | (2006.01) |
| *C08G 65/48* | (2006.01) |
| *C07B 41/02* | (2006.01) |
| *C07B 43/04* | (2006.01) |
| *C07B 43/08* | (2006.01) |
| *C07B 41/04* | (2006.01) |
| *C08G 63/91* | (2006.01) |
| *C08F 120/32* | (2006.01) |
| *C07D 301/02* | (2006.01) |
| *C07B 41/08* | (2006.01) |

(52) U.S. Cl.
CPC ........... *C01B 31/0469* (2013.01); *C01B 31/043* (2013.01); *C07D 301/02* (2013.01); *C08G 65/48* (2013.01)

(58) Field of Classification Search
CPC C01B 31/04; C01B 31/0407; C01B 31/0415; C01B 2204/00; C01B 2204/02; C01B 2204/04; C01B 2204/06; C01B 2204/065; C01B 2204/20; C01B 2204/22; C01B 2204/24; C01B 2204/28; C01B 2204/30; C01B 2204/32
USPC .......................................................... 423/448
See application file for complete search history.

(56) References Cited

U.S. PATENT DOCUMENTS

| | | | | |
|---|---|---|---|---|
| 5,188,090 | A * | 2/1993 | Griggs | 126/247 |
| 5,385,298 | A * | 1/1995 | Griggs | 237/1 R |
| 6,627,784 | B2 * | 9/2003 | Hudson et al. | 588/320 |
| 6,872,330 | B2 | 3/2005 | Mack et al. | |
| 7,071,258 | B1 | 7/2006 | Jang et al. | |
| 7,824,651 | B2 | 11/2010 | Zhamu et al. | |
| 2002/0054995 | A1* | 5/2002 | Mazurkiewicz | 428/364 |
| 2009/0155578 | A1* | 6/2009 | Zhamu et al. | 428/336 |
| 2010/0147188 | A1* | 6/2010 | Mamak et al. | 106/31.13 |
| 2011/0017585 | A1* | 1/2011 | Zhamu et al. | 204/157.42 |

OTHER PUBLICATIONS

Shen, et al., Preparation of graphene by jet cavitation, Nanotechnology 2011; 22: 365306 (pp. 1-7).*

* cited by examiner

*Primary Examiner* — Daniel C McCracken

(57) ABSTRACT

The invention provides a method of producing a graphene material from a starting graphitic material. In an embodiment, the method comprises: (a) dispersing the starting graphitic material in a liquid medium to form a graphite suspension; and (b) introducing the graphite suspension into a hydrodynamic cavitation reactor that generates and collapses cavitation or bubbles in the liquid medium to exfoliate and separate graphene planes from the starting graphitic material for producing the graphene material. The process is fast (minutes as opposed to hours or days of conventional processes), environmentally benign, and highly scalable. The reactor can concurrently perform the functions of graphene production, chemical functionalization, dispersion, and mixing with a polymer to make a composite.

35 Claims, 5 Drawing Sheets

PRODUCTION OF GRAPHENE MATERIALS IN A CAVITATING FLUID

FIELD OF THE INVENTION

The present invention relates to a method of producing graphene materials, including pristine graphene, graphene oxide, graphene halogenide (fluoride, bromide, chloride, and iodide), hydrogenated graphene, nitrogenated graphene, and functionalized graphene.

BACKGROUND

A single-layer graphene sheet is composed of carbon atoms occupying a two-dimensional hexagonal lattice. Multi-layer graphene is a platelet composed of more than one graphene plane. Individual single-layer graphene sheets and multi-layer graphene platelets are herein collectively called nano graphene platelets (NGPs) or graphene materials. Single-layer and multi-layer NGPs include pristine graphene (essentially >99% of carbon atoms), slightly oxidized graphene (<5% by weight of oxygen), graphene oxide (≥5% by weight of oxygen), slightly fluorinated graphene (<5% by weight of fluorine), graphene fluoride ((≥5% by weight of fluorine), other halogenated graphene, hydrogenated graphene, and chemically functionalized graphene.

NGPs have been found to have a range of unusual physical, chemical, and mechanical properties. For instance, graphene was found to exhibit the highest intrinsic strength and highest thermal conductivity of all existing materials. Although practical electronic device applications for graphene (e.g., replacing Si as a backbone in a transistor) are not envisioned to occur within the next 5-10 years, its application as a nano filler in a composite material and an electrode material in energy storage devices is imminent. The availability of processable graphene sheets in large quantities is essential to the success in exploiting composite, energy, and other applications for graphene.

Our research group was among the first to discover graphene [B. Z. Jang and W. C. Huang, "Nano-scaled Graphene Plates," U.S. patent application Ser. No. 10/274,473, submitted on Oct. 21, 2002; now U.S. Pat. No. 7,071,258 (Jul. 4, 2006)]. The processes for producing NGPs and NGP nanocomposites were recently reviewed by us [Bor Z. Jang and A Zhamu, "Processing of Nano Graphene Platelets (NGPs) and NGP Nanocomposites: A Review," J. Materials Sci. 43 (2008) 5092-5101]. Four main prior-art approaches have been followed to produce NGPs. Their advantages and shortcomings are briefly summarized as follows:

Approach 1: Chemical Formation and Reduction of Graphite Oxide (GO) Sheets or Platelets The first approach (FIG. 1) entails treating natural graphite powder with an intercalant and an oxidant (e.g., concentrated sulfuric acid and nitric acid, respectively) to obtain a graphite intercalation compound (GIC) or, actually, graphite oxide (GO). Prior to intercalation or oxidation, graphite has an inter-graphene plane spacing of approximately 0.335 nm ($L_d=\frac{1}{2} d_{002}=0.335$ nm). With an intercalation and oxidation treatment, the inter-graphene spacing is increased to a value typically greater than 0.6 nm. This is the first expansion stage experienced by the graphite material during this chemical route. The obtained GIC or GO is then subjected to further expansion (often referred to as exfoliation) using either a thermal shock exposure or a solution-based, ultrasonication-assisted graphene layer exfoliation approach.

In the thermal shock exposure approach, the GIC or GO is exposed to a high temperature (typically 800-1,050° C.) for a short period of time (typically 15 to 60 seconds) to exfoliate or expand the GIC or GO for the formation of exfoliated or further expanded graphite, which is typically in the form of a "graphite worm" composed of graphite flakes that are still interconnected with one another. This thermal shock procedure can produce some separated graphite flakes or graphene sheets, but normally the majority of graphite flakes remain interconnected. Typically, the exfoliated graphite or graphite worm is then subjected to a flake separation treatment using air milling, mechanical shearing, or ultrasonication in water. Hence, approach 1 basically entails three distinct procedures: first expansion (oxidation or intercalation), further expansion (or "exfoliation"), and separation.

In the solution-based separation approach, the expanded or exfoliated GO powder is dispersed in water or aqueous alcohol solution, which is subjected to ultrasonication. It is important to note that in these processes, ultrasonification is used after intercalation and oxidation of graphite (i.e., after first expansion) and typically after thermal shock exposure of the resulting GIC or GO (after second expansion). Alternatively, the GO powder dispersed in water is subjected to an ion exchange or lengthy purification procedure in such a manner that the repulsive forces between ions residing in the inter-planar spaces overcome the inter-graphene van der Waals forces, resulting in graphene layer separations.

There are several major problems associated with this chemical production process:

(1) The process requires the use of large quantities of several undesirable chemicals, such as sulfuric acid, nitric acid, and potassium permanganate or and sodium chlorate.

(2) The chemical treatment process requires a long intercalation and oxidation times, typically 5 hours to five days.

(3) Strong acids consume a significant amount of graphite during this long intercalation/oxidation process by "eating their way into the graphite" (converting graphite into carbon dioxide, which is lost in the process). It is not unusual to lose 20-50% by weight of the graphite material immersed in strong acids and oxidizers.

(4) The thermal exfoliation requires a high temperature (typically 800-1,050° C.) and, hence, is a highly energy-intensive process.

(5) Both heat- and solution-induced exfoliation approaches require a very tedious washing and purification step. For instance, typically 2.5 kg of water is used to wash and recover 1 gram of GIC, producing huge quantities of waste water that need to be properly treated.

(6) In both the heat- and solution-induced exfoliation approaches, the resulting products are GO platelets that must undergo a further chemical reduction treatment to reduce the oxygen content. Typically even after reduction, the electrical conductivity of GO platelets remains much lower than that of pristine graphene. Furthermore, the reduction procedure often involves the utilization of toxic chemicals, such as hydrazine.

(7) Furthermore, the quantity of intercalation solution retained on the flakes after draining may range from 20 to 150 parts of solution by weight per 100 parts by weight of graphite flakes (pph) and more typically about 50 to 120 pph. During the high-temperature exfoliation, the residual intercalate species retained by the flakes decompose to produce various species of sulfuric and nitrous compounds (e.g., $NO_x$ and $SO_x$), which are undesirable. The effluents require expensive remediation procedures in order not to have an adverse environmental impact.

The present invention was made to address these issues.

Approach 2: Direct Formation of Pristine Nano Graphene Platelets

In 2002, our research team succeeded in isolating single-layer and multi-layer graphene sheets from partially carbonized or graphitized polymeric carbons, which were obtained from a polymer or pitch precursor [[B. Z. Jang and W. C. Huang, "Nano-scaled Graphene Plates," U.S. patent application Ser. No. 10/274,473, submitted on Oct. 21, 2002; now U.S. Pat. No. 7,071,258 (Jul. 4, 2006)]. Mack, et al ["Chemical manufacture of nanostructured materials" U.S. Pat. No. 6,872,330 (Mar. 29, 2005)] developed a process that involved intercalating graphite with potassium melt and contacting the resulting K-intercalated graphite with alcohol, producing violently exfoliated graphite containing NGPs. The process must be carefully conducted in a vacuum or an extremely dry glove box environment since pure alkali metals, such as potassium and sodium, are extremely sensitive to moisture and pose an explosion danger. This process is not amenable to the mass production of NGPs.

Pristine graphene may also be produced by a method called "direct ultrasonication," which is also developed earlier by our research team [A. Zhamu, et al., "Method of Producing Exfoliated Graphite, Flexible Graphite, and Nano-Scaled Graphene Plates," U.S. Pat. No. 7,824,651 (Nov. 2, 2010)]. This method comprises (a) dispersing particles of graphite in a liquid medium containing therein a surfactant or dispersing agent to obtain a stable suspension or slurry; and (b) exposing the suspension or slurry to ultrasonic waves to produce separated nano-scaled graphene platelets. This direct ultrasonication appears to produce a relatively low amount of graphene materials per unit volume per unit reaction time (low production yield rate).

Approach 3: Epitaxial Growth and Chemical Vapor Deposition of Nano Graphene Sheets on Inorganic Crystal Surfaces Small-scale production of ultra-thin graphene sheets on a substrate can be obtained by thermal decomposition-based epitaxial growth and a laser desorption-ionization technique. Single-layer graphene films may also be produced by catalytic chemical vapor deposition (CVD) that involves thermal conversion of hydrocarbon gas molecules to carbon species that deposit onto the surface of a catalytic metal foil, such as Cu or Ni.

Epitaxial films of graphite or CVD graphene with only one or a few atomic layers are of technological and scientific significance due to their peculiar characteristics and great potential as a device substrate. However, these processes are not suitable for mass production of isolated graphene sheets for composite materials and energy storage applications. These processes are also very slow and very expensive.

Approach 4: The Bottom-Up Approach (Synthesis of Graphene from Small Molecules)

Yang, et al. ["Tow-dimensional Graphene Nano-ribbons," J. Am. Chem. Soc. 130 (2008) 4216-17] synthesized nano graphene sheets with lengths of up to 12 nm using a method that began with Suzuki-Miyaura coupling of 1,4-diiodo-2,3,5,6-tetraphenyl-benzene with 4-bromophenylboronic acid. The resulting hexaphenylbenzene derivative was further derivatized and ring-fused into small graphene sheets. This is a slow process that thus far has produced very small graphene sheets. The scalability of this process has yet to be validated.

Hence, an urgent need exists to have a graphene production process that requires a reduced amount of undesirable chemical, shortened process time, less energy consumption, lower degree of graphene oxidation, reduced or eliminated effluents of undesirable chemical species into the drainage (e.g., sulfuric acid) or into the air (e.g., $SO_2$ and $NO_2$). The process should be able to produce more pristine (less oxidized and, hence, less damaged), more electrically conductive, and larger/wider graphene sheets.

SUMMARY OF THE INVENTION

The present invention provides a strikingly simple, fast, scalable, environmentally benign, and cost-effective method that meets the aforementioned needs. This method of producing graphene from a graphitic material comprises subjecting a suspension (containing a graphitic material dispersed in a liquid medium) to shockwaves produced by cavitation and collapse of micro-bubbles generated in a hydrodynamic cavitation reactor. After graphite powder is dispersed in a liquid medium, the resulting suspension is exposed to cavitation treatments in a hydrodynamic cavitation reactor. This is essentially a single-step process. Typically, in less than 5-10 minutes, graphite is highly exfoliated. This process is stunningly fast, effective, and powerful.

In one embodiment, the invention provides a method of producing pristine or non-oxidized graphene directly from a starting graphitic material that has not been previously intercalated or oxidized (a pristine graphitic material). The method comprises: (a) dispersing the starting pristine graphitic material in a liquid medium to form a graphite suspension; and (b) introducing the graphite suspension into a hydrodynamic cavitation reactor that generates and collapses cavitation or bubbles in the fluid medium to exfoliate and separate graphene planes from the graphitic material for producing the pristine or non-oxidized graphene.

In a preferred embodiment, the hydrodynamic cavitation reactor includes a housing defining a cylindrical chamber, a cylindrical rotor rotatably mounted in the chamber, bores in a peripheral surface of the rotor, and a cavitation zone defined between the peripheral surface of the rotor and an interior wall of the chamber. The step of introducing the suspension comprises passing the graphite suspension through the cavitation zone as the rotor rotates. In another preferred embodiment, the hydrodynamic cavitation reactor operates by passing a liquid through a constricted channel at a specific velocity to produce cavitation or micro-bubbles.

The liquid medium can be simply water, an alcohol, or a water-alcohol mixture. In one embodiment, the liquid medium contains water and a surfactant. The surfactant may be selected from the group consisting of anionic surfactants, nonionic surfactants, cationic surfactants, amphoteric surfactants, silicone surfactants, fluoro-surfactants, polymeric surfactants, sodium hexametaphosphate, sodium lignosulphonate, poly(sodium 4-styrene sulfonate), sodium dodecylsulfate, sodium sulfate, sodium phosphate, sodium sulfonate, and combinations thereof.

In an embodiment, the liquid medium contains an organic solvent. A particularly useful solvent is selected from N-methylpyrrolidone (NMP), N,N-Dimethylacetamide (DMA), γ-butyrolactone (GBL), 1,3-dimethyl-2-imidazolidinone (DMEU), or a combination thereof. The liquid medium preferably contains an organic solvent having a surface free energy that enables wetting of the liquid medium on a graphene plane of the starting graphitic material.

The liquid medium may contain an ionic liquid, which is an ionic salt having a melting temperature lower than 100° C., preferably a room temperature ionic liquid (RTIL) having a melting point lower than room temperature (25° C.). The liquid medium may contain an acid, preferably a weak acid selected from formic acid, acetic acid, nitric acid, maleic acid, or carboxylic acid. The controlled cavitation reactor is preferably operated at a temperature lower than 100° C., more preferably lower than 50° C.

The starting graphitic material may be selected from natural graphite, synthetic graphite, highly oriented pyrolytic graphite, meso-carbon micro-bead, coke (e.g. needle coke), graphitized meso-phase carbon, graphitized soft carbon, exfoliated graphite, expanded graphite, carbon or graphite fiber, carbon or graphitic nano-fiber, or a combination thereof. Any of the aforementioned graphitic materials can be oxidized, fluorinated, chlorinated, nitrogenated, hydrogenated, etc. before the material is dispersed to form a suspension and introduced into a hydrodynamic cavitation reactor.

Under favorable conditions, the method is capable of producing essentially all single-layer graphene. In an embodiment, the produced graphene material contains at least 80% single-layer graphene sheets. In many cases, the product mass contains both single-layer graphene and multi-layer graphene sheets (typically less than 20 layers and more typically less than 10 layers of graphene plane of carbon atoms).

The invention also provides a method of producing and, concurrently, chemically functionalizing graphene material directly from a starting graphitic material that has not been previously intercalated or oxidized. The method comprises: (a) dispersing the starting graphitic material in a liquid medium to form a graphite suspension, wherein the liquid medium contains therein an oxidizing agent or a chemical functionalization agent; and (b) introducing the graphite suspension into a controlled cavitation reactor that generates and collapses cavitation or bubbles in the liquid medium to produce shock waves, wherein the graphite suspension is exposed to shockwaves for producing and chemically oxidizing or functionalizing the graphene material.

The method as herein disclosed may further comprise a step of converting the graphene material (which is naturally dispersed in the liquid medium upon cavitation) into a powder, paper, or mat form.

In an embodiment, the liquid medium contains a graphitic material (a pristine, fluorinated, nitrogenated, intercalated, expanded, or exfoliated version, etc. of a graphitic material) and further contains therein an oxidizing agent or a chemical functionalization agent and the controlled cavitation reactor generates and collapses cavitation or bubbles in the liquid medium to produce the graphene material and, concurrently, oxidize or chemically functionalize the graphene material to produce a graphene oxide or a chemically functionalized graphene material dispersed in the liquid medium. The method may further comprise a step of converting the chemically functionalized graphene material dispersed in the liquid medium into a paper or mat form.

In another embodiment, the liquid medium further contains therein a monomer, oligomer, or polymer and the controlled cavitation reactor generates and collapses cavitation or bubbles in the liquid medium to produce the graphene material, disperse the graphene material in the liquid medium, and disperse or dissolve the monomer, oligomer, or polymer in the liquid medium to form a precursor composite suspension. The method may further comprise a step of converting the precursor composite suspension into a solid graphene-polymer nanocomposite.

In yet another embodiment, the liquid medium further contains therein an oxidizing agent or a chemical functionalization agent and a monomer, oligomer, or polymer. The hydrodynamic cavitation reactor generates and collapses cavitation or bubbles in the liquid medium to produce the graphene material, to chemically functionalize the graphene material, and to dissolve or disperse the monomer, oligomer, or polymer in the liquid medium to produce a precursor composite suspension. The method may further comprise a step of converting the precursor composite suspension into a graphene-polymer nanocomposite. The monomer or oligomer may be polymerized in the cavitation reactor.

In all the versions of the invented method, the liquid medium may be a mixture containing an acid and an oxidizing agent. The liquid medium may contain a carboxylic acid selected from the group consisting of aromatic carboxylic acid, aliphatic or cycloaliphatic carboxylic acid, straight chain or branched chain carboxylic acid, saturated and unsaturated monocarboxylic acids, dicarboxylic acids and polycarboxylic acids that have 1-10 carbon atoms, alkyl esters thereof, and combinations thereof. The carboxylic acid may be selected from the group consisting of saturated aliphatic carboxylic acids of the formula $H(CH_2)_nCOOH$, wherein n is a number of from 0 to 5, including formic, acetic, propionic, butyric, pentanoic, and hexanoic acids, anhydrides thereof, reactive carboxylic acid derivatives thereof, and combinations thereof.

Still another embodiment of the present invention is a method of producing a graphene material from a starting graphitic material that is an intercalated, oxidized, halogenated, exfoliated, or expanded graphite. The expanded graphite typically refers to a material obtained by breaking up exfoliate graphite (graphite worms) to produce graphite flakes that are typically thicker than 100 nm. The method comprises: (a) dispersing the starting graphitic material in a liquid medium to form a graphite suspension; and (b) introducing the graphite suspension into a controlled cavitation reactor that generates and collapses cavitation or bubbles in the fluid medium to exfoliate and separate graphene planes from the starting graphitic material for producing the graphene material that is dispersed in the liquid medium. The method may further comprise a step of converting the graphene material dispersed in the liquid medium into a powder, paper, or mat form.

In an embodiment, the starting graphitic material contains exfoliated graphite or expanded graphite, the liquid medium further contains therein an oxidizing agent, and the hydrodynamic cavitation reactor is operated to produce and oxidize the graphene material to produce a graphene oxide material dispersed in the liquid medium. The graphene oxide may be made into a powder form by removing (e.g. vaporizing) the liquid medium.

The liquid medium may further contain therein a chemical functionalization agent and the controlled cavitation reactor generates and collapses cavitation or bubbles in the liquid medium to concurrently produce and chemically functionalize the graphene material, which is dispersed in the liquid medium. The method may further comprise a step of converting the chemically functionalized graphene material dispersed in the liquid medium into a powder, paper, or mat form.

In a desirable embodiment, the liquid medium further contains therein a monomer, oligomer, or polymer and the controlled cavitation reactor generates and collapses cavitation or bubbles in the liquid medium to produce the graphene material, disperse the graphene material in the liquid medium, and disperse or dissolve the monomer, oligomer, or polymer in the liquid medium to form a precursor composite suspension. The method may further comprise a step of converting the precursor composite suspension into a graphene-polymer nanocomposite.

The inventive method has the following features or advantages as compared to other methods of graphene production:
1) The method combines exfoliation and separation of graphene sheets in one step, dramatically shortening the time to produce graphene.
2) In the presence of a chemical functional group-containing species, the method is also capable of chemically functionalizing the graphene sheets as produced. Graphene production and functionalization are essentially combined into one step.
3) A faster method also implies reduced loss of starting graphite material otherwise caused by excessive chemical reactions of acid/oxidizer with graphite (as in a conventional chemical method), eating away (consuming) graphite and chemicals (acid and/or oxidizer) to generate CO and $CO_2$, etc. Thus, the inventive method provides a higher graphene yield and significantly reduces the amount of chemicals used.

4) The method also enables the use of non-toxic liquid mediums (e.g. water) or more environmentally benign chemicals (e.g. alcohol).

5) The method can make use of practically any liquid medium and the process also naturally disperses the resulting graphene sheets in such a liquid medium to form a graphene-liquid suspension as a precursor to a final product (e.g. graphene paper or graphene mat). In other words, this method combines exfoliation, separation, and dispersion in a single step.

6) A monomer, oligomer, polymer can be dissolved in the liquid medium before, during, and after graphene production, leading to the preparation of precursor graphene-polymer composite suspension, which can be readily converted into a composite structure (e.g. casting into a composite film and removing the liquid medium to form a solid graphene-polymer composite).

7) A wide variety of starting graphitic materials can be used in the inventive method, including the pristine version thereof (the graphitic materials that have never been exposed to intercalation or oxidation, etc.), the intercalated, oxidized, fluorinated, brominated, chlorinated, iodized, nitrogenated, hydrogenated, expanded, exfoliated, and chemically functionalized versions of a graphitic material selected from natural graphite, synthetic graphite, highly oriented pyrolytic graphite, meso-carbon micro-bead, coke (e.g. needle coke), graphitized meso-phase carbon, carbon or graphite fiber, carbon or graphitic nano-fiber, or a combination thereof.

8) No known method of graphene production is as versatile or powerful as the presently invented method.

DETAILED DESCRIPTION OF PREFERRED EMBODIMENTS

Figure 1:
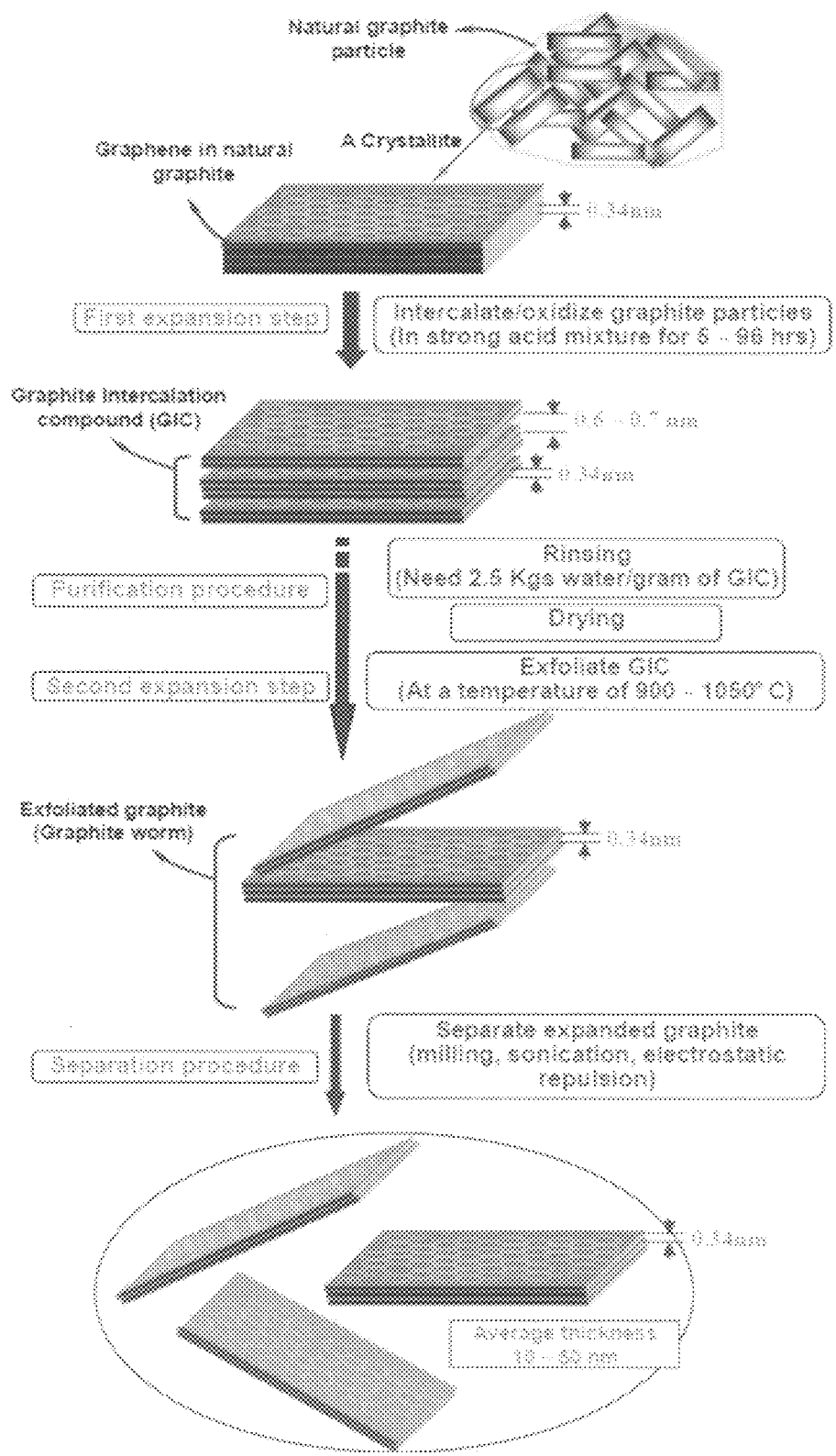
FIG. 1 A flow chart showing the most commonly used prior art process of producing highly oxidized NGPs that entails tedious chemical oxidation/intercalation, rinsing, and high-temperature exfoliation procedures.

Carbon materials can assume an essentially amorphous structure (glassy carbon), a highly organized crystal (graphite), or a whole range of intermediate structures that are characterized in that various proportions and sizes of graphite crystallites and defects are dispersed in an amorphous matrix. Typically, a graphite crystallite is composed of a number of graphene sheets or basal planes that are bonded together through van der Waals forces in the crystallographic c-axis direction, the direction perpendicular to the basal plane. These graphite crystallites are typically sub-micron- or nanometer-sized. The graphite crystallites are dispersed in or connected by crystal defects or amorphous phases in a graphite particle, which can be a graphite flake, carbon/graphite fiber segment, carbon/graphite whisker, or carbon/graphite nano-fiber.

One preferred specific embodiment of the present invention is a method of producing a nano graphene platelet (NGP) material that is essentially composed of a sheet of graphene plane (single-layer graphene) or multiple graphene planes stacked and bonded together (typically, on an average, up to 30 sheets per multi-layer graphene). Each graphene plane, also referred to as a basal plane, comprises a two-dimensional hexagonal structure of carbon atoms. Each platelet or sheet has a length and a width parallel to the graphite plane and a thickness orthogonal to the graphite plane. By definition, the thickness of an NGP is 100 nanometers (nm) or smaller, with a single-sheet oxygen-free NGP being as thin as 0.34 nm (single-layer graphene oxide can be from 0.4 to 1.2 nm in thickness). However, most of the NGPs produced are less than 10 nm in thickness (less than 30 layers or 30 graphene planes), mostly less than 10 nm, and most typically less than 3 nm (or 10 graphene planes, commonly referred to as few-layer graphene).

Generally speaking, a method has been developed for concurrently exfoliating and separating a layered or laminar graphite material to produce a graphene material. The method does not involve the use of an intercalation agent (such as K or sulfuric acid), although the method is applicable to intercalated graphite or intercalated graphite oxide compounds as well.

In one embodiment, the invention provides a method of producing pristine or non-oxidized graphene directly from a starting graphitic material that has not been previously intercalated or oxidized (hence, a pristine graphitic material). The method comprises: (a) dispersing the starting graphitic material in a liquid medium to form a graphite suspension; and (b) introducing the graphite suspension into a controlled cavitation reactor that hydrodynamically generates and collapses cavitation or bubbles in the fluid medium to produce shock waves, wherein the graphite suspension is exposed to shock-waves for producing the pristine or non-oxidized graphene. The same method can be used to produce graphene oxide sheets from oxidized graphite materials or graphene fluoride sheets from fluorinated graphite, etc.

With a sufficient level of hydrodynamic cavitation power and sufficient length of time, one can easily produce a mass wherein more than 80% of NGPs are single-layer versions of graphene, graphene oxide, or graphene fluoride, etc. Quite often, essentially all graphene materials are single-layer NGPs. The length and width of a NGP are typically between 200 nm and 20 μm, but could be longer or shorter.

Figure 3A:
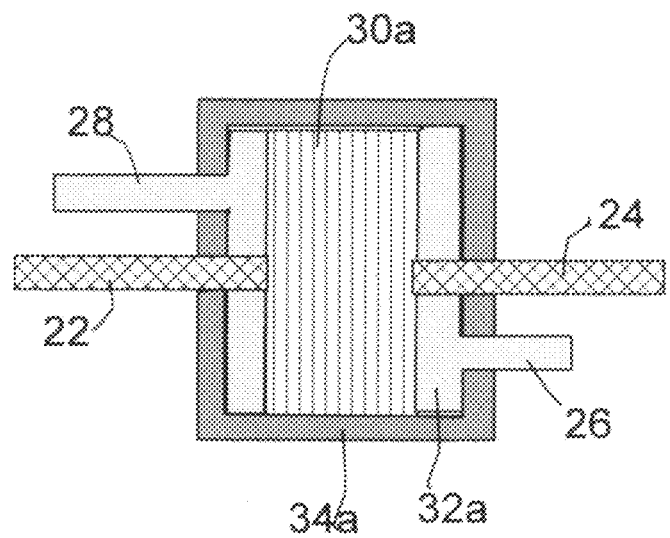
FIG. 3 (A) Schematic of a hydrodynamic cavitation reactor and (B) schematic of the rotator portion of the reactor.
Figure 3B:
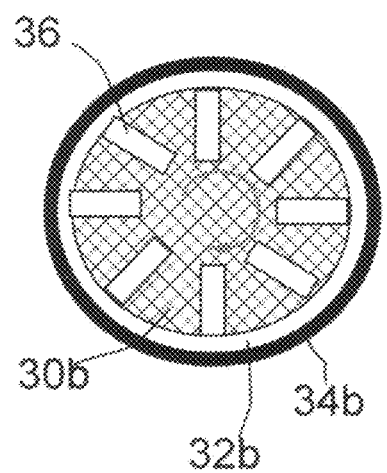

In a preferred embodiment, as illustrated in FIGS. 3(A) and 3(B), the hydrodynamic cavitation reactor includes a housing (34a or 34b) defining a cylindrical chamber (32a or 32b), a cylindrical rotor (30a or 30b) rotatably mounted in the chamber, bores (e.g. 36) in a peripheral surface of the rotor, and a cavitation zone defined between the peripheral surface of the rotor and an interior wall of the chamber. The step of introducing the suspension comprises passing the graphite suspension from an inlet 26, through the cavitation zone as the rotor rotates, and exiting through an outlet 28. The rotor 30a is driven by a motor via shaft 22 and/or 24. The generation and collapse of the cavitation or bubbles produce high-intensity shock waves.

Several techniques can be used to induce cavitation in a liquid: acoustic (ultrasound-induced), hydrodynamic (or generated with laser light), accelerated particles, an electrical discharge or steam injection. Hydrodynamic cavitation comprises the nucleation, fluid vaporization and growth, pulsation (if any), and collapse of bubbles which occurs in a flowing fluid as a result of a decrease and subsequent increase in its static pressure. By contrast, the acoustic- or ultrasound-induced cavitation is not hydrodynamic cavitation and is not included in the hydrodynamic cavitation as herein discussed. It may be noted that the so-called direct ultrasonication for graphene production involves sending ultrasound waves from a piezoelectric transducer into a fluid and the dispersed graphite particles are exposed to the sound waves (tensile and compressive waveforms) that expand and exfoliate graphite. Even though liquid cavitation could possibly occur under favorable ultrasonication conditions, there was no prior teaching to suggest that cavitation occurred during ultrasonication production of graphene, or that ultrasound-induced cavitation was capable of producing graphene sheets. Further, ultrasonic wave-induced cavitation, if any, is not hydrodynamic cavitation.

Broadly speaking, hydrodynamic cavitation is a process of vaporization, bubble generation, and bubble implosion, which occurs in a flowing liquid as a result of a decrease and subsequent increase in pressure. In general, cavitation will only occur if the pressure declines to some point below the saturated vapor pressure of the liquid and subsequent recovery above the vapor pressure. Hydrodynamic cavitation can be produced by passing a liquid through a constricted channel at a specific velocity or by mechanical rotation of an object through a liquid as described above. In the case of the constricted channel and based on the specific geometry of the system, the combination of pressure and kinetic energy can create the hydrodynamic cavitation cavern downstream of the local constriction generating high energy cavitation bubbles.

The process of bubble generation, and the subsequent growth and collapse of the cavitation bubbles, results in very high energy densities and potentially results in very high temperatures and pressures at the surface of the bubbles for a very short time. However, the overall liquid medium environment remains at ambient conditions. When uncontrolled, cavitation can be damaging due to excessively high local temperatures or pressures. The design, as schematically shown in FIGS. 3(A) and (B), enables controlled cavitation of a liquid medium.

In an embodiment, the first step of the inventive method may involve preparing a graphitic material powder containing fine graphite particulates (granules) or flakes, short segments of carbon fiber or graphite fiber, carbon or graphite whiskers, carbon or graphitic nano-fibers, or their mixtures. The length and/or diameter of these graphite particles are preferably less than 0.2 mm (200 µm), further preferably less than 0.01 mm (10 µm). They can be smaller than 1 µm. The graphite particles are known to typically contain sub-micron- and/or nanometer-scaled graphite crystallites with each crystallite being composed of multiple graphene planes.

Although intercalation is not a requirement, we have also investigated the exfoliation and isolation (separation) of intercalated graphite compounds and oxidized graphite at low temperatures (e.g., room temperature). Intercalation of graphite is well-known in the art. A wide range of intercalants have been used; e.g., (a) a solution of sulfuric acid or sulfuric-phosphoric acid mixture, and an oxidizing agent such as hydrogen peroxide and nitric acid and (b) mixtures of sulfuric acid, nitric acid, and manganese permanganate at various proportions. Typical intercalation times are between 2 hours and five days. The resulting acid-intercalated graphite may be subjected to repeated washing and neutralizing steps to produce a laminar compound that is essentially graphite oxide. In other words, graphite oxide can be readily produced from acid intercalation and oxidation of graphite flakes. It is important to emphasize that the presently invented method is applicable to both graphite and graphite oxide that are either un-intercalated or intercalated.

The starting graphitic material (e.g., graphite or graphite oxide particles) is dispersed in a liquid medium (e.g., water, alcohol, or acetone) to obtain a suspension or slurry with the particles being suspended in the liquid medium, which is subjected to hydrodynamically induced cavitation. Preferably, a dispersing agent or surfactant is used to help uniformly disperse particles in the liquid medium. Most importantly, we have surprisingly found that the dispersing agent or surfactant facilitates the exfoliation and separation of the laminar graphite material. Under comparable processing conditions, a graphite suspension sample containing a surfactant in the cavitating liquid medium usually results in much thinner platelets compared to a sample containing no surfactant. It also takes a shorter length of time for a surfactant-containing suspension to achieve a desired platelet dimension.

Surfactants or dispersing agents that can be used include, as examples, anionic surfactants, non-ionic surfactants, cationic surfactants, amphoteric surfactants, silicone surfactants, fluoro-surfactants, and polymeric surfactants. Particularly useful surfactants for practicing the present invention include DuPont's Zonyl series that entails anionic, cationic, non-ionic, and fluoro-based species. Other useful dispersing agents include sodium hexametaphosphate, sodium lignosulphonate (e.g., marketed under the trade names Vanisperse CB and Marasperse CBOS-4 from Borregaard LignoTech), sodium sulfate, sodium phosphate, and sodium sulfonate.

Conventional exfoliation processes for producing graphite worms (as a precursor to graphene platelets) from a graphite material normally include exposing a graphite intercalation compound (GIC) to a high temperature environment, most typically between 850 and 1,050° C. These high temperatures were utilized with the purpose of maximizing the expansion of graphite crystallites along the crystallographic c-axis direction. Unfortunately, this is an energy-intensive process that can also generate undesirable species, such as $SO_2$ and $NO_x$, which are discharged into open air.

In contrast, the presently invented method makes use of a cavitating fluid at a temperature typically from 0° C. to 100° C. Hence, this method obviates the need or possibility to expose the layered graphitic material to a high-temperature, oxidizing environment. Further, the process does not require the use of any undesirable chemical, such as sulfuric acid, and hence requires no subsequent waste water treatment and does not involve releasing undesirable species into open air.

As the suspension passes through a hydrodynamic cavitation reactor, the carrier liquid medium is subjected to "controlled cavitation" which involves micro-bubble formation and collapsing, thereby emitting high-intensity shockwaves. In a preferred embodiment, this reactor contains a specially designed rotor that contains bores in a peripheral surface of the rotor. The spinning action of the rotor generates hydrodynamic cavitation in the rotor cavities away from the metal surfaces. As microscopic cavitation bubbles are produced and collapsed, shockwaves are given off into the liquid which surprisingly can peel off large numbers of graphene sheets from the graphitic material at a very high rate. The specialized rotor has dead-ended cavities. Spinning creates low pressure at the cavity bottoms. The low pressure zones collapse, releasing shockwaves. Cavitation is created in the cavities, not on metal surfaces.

Briefly described, a preferred embodiment of the present invention comprises a unique and highly efficient method of peeling off graphene sheets directly from graphite particles suspended in a cavitating fluid contained in a shockwave reactor, which is capable of mechanically inducing cavitation within the fluid in a controlled manner. The result and goal is to obtain a graphene material that contains single-layer and/or multi-layer graphene sheets directly from a pristine graphite material. In a preferred embodiment and best mode, the invention comprises a method of producing all single-layer or few-layer graphene (no more than 10 layers). The result is a process that virtually combines the functions of graphene plane expansion, exfoliation (peeling-off), and separation (isolation) all in one step.

In a preferred embodiment, the step of inducing cavitation comprises introducing the mixture into a chamber having a rotating disk formed with a plurality of irregularities such as bores. The irregularities on the rotating disk induce cavitation in the mixture. The cavitation also breaks down van der Waals attractions between graphene planes of a graphite particle. The methodology of the invention, in one embodiment, comprises the steps of introducing and entraining air in the form of bubbles into a stream of graphite particles to form a mixture of graphite particles and air bubbles. The mixture is then directed into a cavitating fluid system, which generally comprises a rapidly spinning rotor disposed within a cylindrical chamber within a housing. The rotor is provided with one or more arrays of relatively shallow holes or bores formed around its periphery. A space, herein referred to as a cavitation zone, is formed between the periphery of the rotor and the cylindrical wall of the housing chamber.

Not wishing to be limited by theory, but we would like to offer a scientifically plausible explanation on why the cavitating fluid can perform the functions of producing a graphene material. As the mixture suspension of gas bubbles, graphite particles and liquid medium passes through the cavitation zone, microscopic cavitation bubbles are continuously generated and collapsed within the suspension by the action of the bores on the periphery of the spinning rotor. The collapse of these cavitation bubbles creates violent and continuous cavitation within the gas/fluid mixture in the cavitation zone, and the energy of this cavitation acts to break up the air bubbles within the mixture into ever smaller bubbles or units. Since the minimum size of the air bubbles is not limited, the air bubbles are reduced by the cavitation into millions of substantially microscopic bubbles. Thus, a huge amount of the total surface area of air bubbles is in contact with graphite particles. The increased surface area increases the probability that a gas molecule within an air bubble will come into contact with a graphite particle. Further, because of the relatively violent agitation within the cavitation zone caused by rotor motion and cavitation effects, these microscopic air bubbles are mixed completely and uniformly throughout the suspension, which further enhances the probability of contact between a gas molecule and a graphite particle. Finally, the energy imparted to the suspension by the cavitation within the cavitation zone is more than sufficient to overcome the van der Waals forces between graphene planes within a graphite particle, thereby exfoliating graphene sheets.

As a result of the creation and uniform distribution of micro-bubbles and the breaking of the van der Waals attractions, virtually complete exfoliation of graphene planes can be accomplished within the reactor. However, through extensive and in-depth experimental studies, we have surprisingly observed that breaking-up of the van der Waals forces between graphene planes can be followed by re-stacking of graphene planes (re-formation of van der Waals forces between hexagonal planes of carbon atoms) provided no effective measures are taken to prevent such a re-formation or re-stacking action. This can lead to the formation of incomplete exfoliation and the production of thick graphene platelets. Much to our surprise, we have discovered that the presence of a surfactant in the liquid medium appears to be effective in preventing the re-stacking of graphene planes once exfoliated via the presently invented cavitation effect. It seems that the presence of surfactant molecules readily enables the wetting of exposed graphene planes by water or surfactant molecules, which prevent complete re-stacking of graphene planes. In other words, these water or surfactant molecules now are positioned between graphene planes, an energetically favorable configuration.

Further, the process can be accurately controlled by selecting the rotation rate of the rotor, the amount of air initially introduced into the suspension, and the amount of surfactant such that the complete exfoliation and separation of graphene sheets is accomplished within a minimum time, with a minimum amount of energy, and the required amount of air introduced. The overall result of our investigation is the discovery of a graphene production process that is far more efficient, faster, and more effective than is possible with prior art processes, including chemical oxidation, intercalation, and direct ultrasonication.

In addition to creating ultra-thin NGPs, including single-layer graphene and few-layer graphene, directly from pristine graphite, the cavitating fluid also can perform several totally unexpected functions that are highly desirable and of great utility value:

(1) Homogeneous dispersion of graphene sheets in the liquid medium: The cavitation also enables the resulting graphene platelets to be well dispersed in the very liquid medium, producing a homogeneous suspension. Thus, one major advantage of this approach is that exfoliation, separation, and dispersion of graphene sheets are achieved in a single step. The process may include a further step of converting the suspension to a mat or paper (e.g., using any well-known paper-making process) or a powder form (e.g. by vaporizing the liquid medium).

(2) Concurrent dissolution or dispersion of a monomer, oligomer, or polymer in the same suspension of graphite particles in liquid medium: A monomer, oligomer, or polymer may be added to this suspension to form a mixture suspension that is a precursor to a nanocomposite structure. The process may include a further step of converting the nanocomposite precursor suspension to a nanocomposite solid.

(3) Cavitation-induced polymerization: Hydrodynamic cavitation was also found to be capable of initiating and completing the polymerization of a monomer or oligomer to form a polymer in situ, with graphene sheets well mixed within the polymer solution.

(4) Production and dispersion of ultra-thin graphene sheets from an intercalated, oxidized, or halogenated graphite material, or exfoliated graphite (graphite worms) produced therefrom: a wide variety of graphitic materials can be used as the starting material.

(5) Concurrent chemical functionalization or chemical oxidation of graphene sheets produced. This will be further discussed in later sections of this specification.

If the platelets in a suspension comprise graphene oxide (GO) platelets, the process may further include a step of partially or totally reducing the GO after the formation of the suspension. GO sheets can be reduced by chemical means (e.g. reacting with hydrazine) or by heat (typically at 100-700° C.).

In an embodiment, the resulting platelets, after drying to become a solid powder, may be mixed with a monomer to form a mixture, which can be polymerized to obtain a nanocomposite solid. Alternatively, the platelets can be mixed with a polymer melt to form a mixture that is subsequently solidified to become a nanocomposite solid.

Figure 2A:
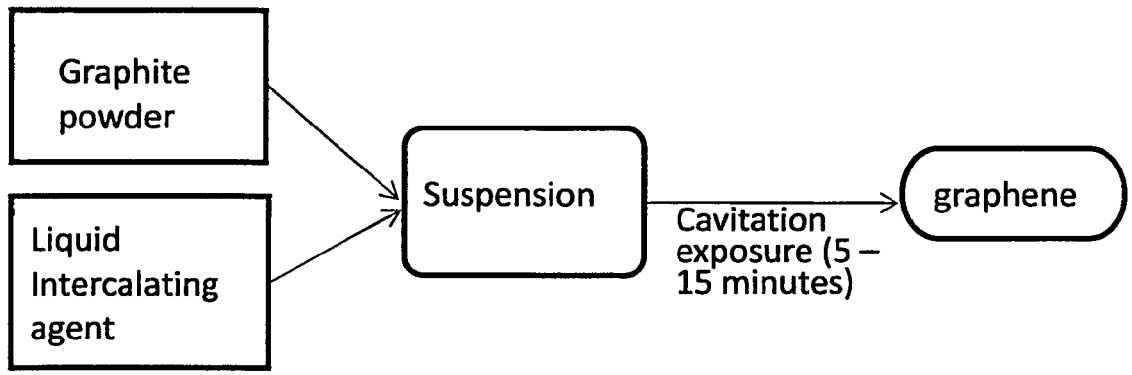
FIG. 2 (A) Flowchart for the presently invented one-step hydrodynamic cavitation process and (B) flowchart for the conventional, multi-step process of producing graphene materials.

The present invention provides a strikingly simple, fast, scalable, environmentally benign, and cost-effective process that avoids essentially all of the drawbacks associated with prior art processes. As schematically illustrated in FIG. 2(A), one preferred embodiment of this method entails subjecting a suspension (containing a graphitic material dispersed in a liquid medium) to a cavitation treatment for a length of time sufficient for producing the graphene material. This is essentially a single-step process. After graphite powder is dispersed in a liquid medium (e.g. water+surfactant), the resulting suspension is immediately exposed to cavitation. In less than 15 minutes (typically less than 5 minutes), graphite can be highly exfoliated, forming mostly single-layer graphene and, in some cases, some few-layer graphene (mostly no more than 5 layers). This process is stunningly short and elegantly simple.

Figure 2B:
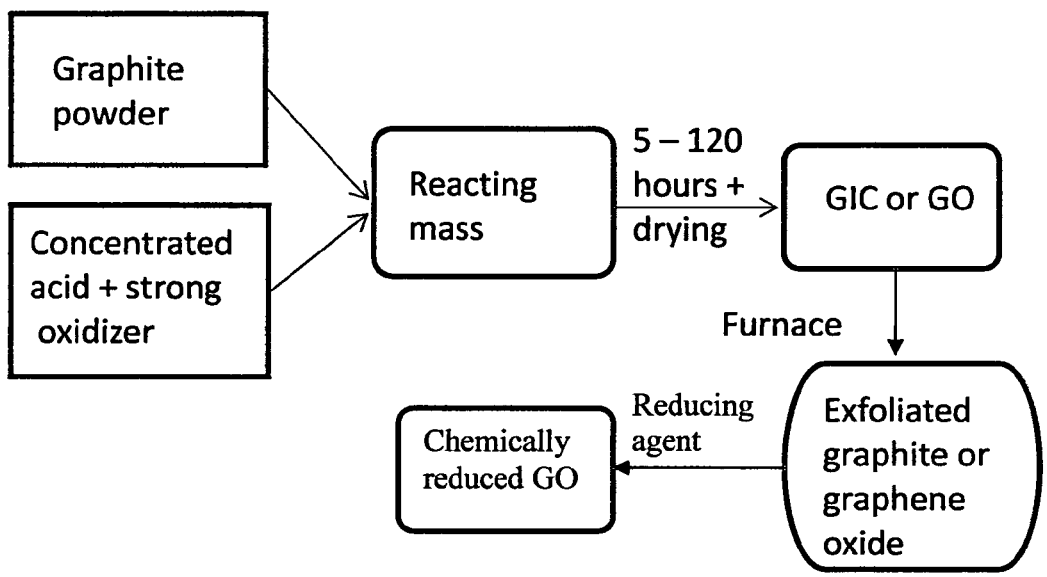

In contrast, as shown in FIG. 1 and FIG. 2(B), the prior art chemical processes typically involve immersing graphite powder in a mixture of concentrated sulfuric acid, nitric acid, and an oxidizer, such as potassium permanganate or sodium perchlorate, forming a reacting mass that requires typically 5-120 hours to complete the chemical intercalation/oxidation reaction. Once the reaction is completed, the slurry is subjected to repeated steps of rinsing and washing with water and then subjected to drying treatments to remove water. The dried powder, referred to as graphite intercalation compound (GIC) or graphite oxide (GO), is then subjected to a thermal shock treatment. This can be accomplished in two ways. One is to expose the GIC to a furnace pre-set at a temperature of typically 800-1100° C. (more typically 950-1050° C.). The other is to expose the GIC to microwave heating.

It is also significant to understand that the GICs obtained by all prior art chemical oxidation processes necessarily contain sulfuric acid and nitric acid in the inter-graphene spaces and, hence, necessarily involve the decomposition of $H_2SO_4$ and $HNO_3$ to produce volatile gases (e.g. $NO_x$ and $SO_x$) during their subsequent heating or thermal exfoliation process. The $NO_x$ and $SO_x$ are highly regulated species that can potentially pose some environmental issues. In contrast, our new process does not involve exposing GIC to a high temperature and, hence, does not generate any of these volatile species. Clearly, the presently invented process is not an obvious variant of the thermal exfoliation of GIC. The GIC and exfoliated graphite have a long history (>50 years) and over such a long period of time, the prior art workers have always believed that thermal exfoliation of graphite must go through a tedious chemical intercalation/oxidation of graphite. The need to use combined strong acids and oxidizers to intercalate and oxidize graphite for an extended period of time to produce the so-called GIC or "expandable graphite" is now completely avoided.

Additionally, our new process does not require a mixture of concentrated sulfuric acid and fuming nitric acid and/or potassium permanganate. Dilute acids or weaker acids, such as acetic acid and formic acid, can be a very effective liquid medium for cavitation. Further, we can use just an acid alone or an oxidizer alone, although we can also use a combination. These are very surprising and have defied the expectations of those who work in exfoliated graphite or graphene industry. Furthermore, no subsequent high temperature exposure for exfoliation is required since exfoliated graphite or graphene is directly produced with a simple cavitation treatment of graphite dispersed in a liquid medium.

Although the mechanisms remain incompletely understood, this revolutionary process of the present invention appears to essentially combine the required functions of graphene plane expansion, exfoliation, and separation of graphene sheets from one another into one single step. The whole process can take less than 15 minutes. This is absolutely stunning, a shocking surprise to even those top scientists and engineers or those of extraordinary ability in the art.

From the environmental protection perspective, the practice of mixing two or three chemicals together (e.g. mixing sulfuric acid, nitric acid, and/or potassium permanganate) can be troublesome since it would make the recovery, separation, and re-use of chemicals so much more difficult. This is more than just a cost issue, but a larger environmental and societal issue and an industrial scalability issue. The significance of our surprising discovery to use a single-component liquid medium in a single-step process should not be underestimated or ignored.

The liquid medium is preferably water or alcohol, but it can be an acid selected from sulfuric acid, sulfonic acid, formic acid, acetic acid, or nitric acid. There is no particular constraint on the type of acid that can be used. For instance, the acid can be an environmentally benign carboxylic acid. The carboxylic acid, containing only C, H, and O atoms, may be selected from the group consisting of aromatic carboxylic acid, aliphatic or cycloaliphatic carboxylic acid, straight chain or branched chain carboxylic acid, saturated and unsaturated monocarboxylic acids, dicarboxylic acids and polycarboxylic acids that have 1-10 carbon atoms, alkyl esters thereof, and combinations thereof. Preferably, the carboxylic acid is selected from the group consisting of saturated aliphatic carboxylic acids of the formula $H(CH_2)_n COOH$, wherein n is a number of from 0 to 5, including formic, acetic, propionic, butyric, pentanoic, and hexanoic acids, anydrides thereof, reactive carboxylic acid derivatives thereof, and combinations thereof. In place of the carboxylic acids, the anhydrides or reactive carboxylic acid derivatives such as alkyl esters can also be employed. Representative of alkyl esters are methyl formate and ethyl formate. The most preferred carboxylic acids are formic acid and acetic acid.

Representative of dicarboxylic acids are aliphatic dicarboxylic acids having 2-12 carbon atoms, in particular oxalic acid, fumaric acid, malonic acid, maleic acid, succinic acid, glutaric acid, adipic acid, 1,5-pentanedicarboxylic acid, 1,6-hexanedicarboxylic acid, 1,10-decanedicarboxylic acid, cyclohexane-1,4-dicarboxylic acid and aromatic dicarboxylic acids such as phthalic acid or terephthalic acid. Representative of alkyl esters are dimethyl oxylate and diethyl oxylate. Representative of cycloaliphatic acids is cyclohexane carboxylic acid and of aromatic carboxylic acids are benzoic acid, naphthoic acid, anthranilic acid, p-aminobenzoic acid, salicylic acid, o-, m- and p-tolyl acids, methoxy and ethoxybenzoic acids, acetoacetamidobenzoic acids and, acetamidobenzoic acids, phenylacetic acid and naphthoic acids. Representative of hydroxy aromatic acids are hydroxybenzoic acid, 3-hydroxy-1-naphthoic acid, 3-hydroxy-2-naphthoic acid, 4-hydroxy-2-naphthoic acid, 5-hydroxy-1-naphthoic acid, 5-hydroxy-2-naphthoic acid, 6-hydroxy-2-naphthoic acid and 7-hydroxy-2-naphthoic acid. Among the polycarboxylic acids, citric acid is preferred due to its availability and low cost.

The presently invented process does not involve the production of GIC and, hence, does not require the exfoliation of GIC at a high exfoliation temperature (e.g. 800-1,050° C.). This is another major advantage from environmental protection perspective. The prior art processes require the preparation of dried GICs containing sulfuric acid and nitric acid intentionally implemented in the inter-graphene spaces and, hence, necessarily involve the decomposition of $H_2SO_4$ and $HNO_3$ to produce volatile gases (e.g. $NO_x$ and $SO_x$) that are highly regulated environmental hazards. The presently invented process completely obviates the need to decompose $H_2SO_4$ and $HNO_3$ and, hence, is environmentally benign. No undesirable gases are released into the atmosphere during the combined graphite expansion/exfoliation/separation process of the present invention.

Another surprising result of the present study is the observation that a wide variety of carbonaceous and graphitic materials can be directly cavitation-treated to produce graphene. This material may be selected from natural graphite, synthetic graphite, highly oriented pyrolytic graphite, meso-carbon micro-bead, graphitized meso-phase carbon, graphitized soft carbon, coke, graphite fiber, graphitic nano-fiber, graphite oxide, graphite fluoride, chemically modified graphite, exfoliated graphite, or a combination thereof. This is surprising based on the observation that several types of graphitic materials (e.g. carbon fibers, graphite fibers, carbon nano-fibers, etc.) have a hard-shell structure enclosing a core structure composed of stacks of graphene sheets. These hard skins are known to be highly impermeable to chemicals. This is in contrast to the natural graphite and some artificial graphite that have graphene edges exposed to chemicals and permeable to chemicals.

The presently invented process is capable of producing single-layer graphene sheets even from these hard-skinned graphitic materials. In many examples, the graphene material produced contains at least 80% single-layer graphene sheets. The graphene produced can contain pristine graphene, oxidized graphene, graphene fluoride, chlorinated graphene, nitrogenated graphene, hydrogenated graphene, or functionalized graphene, etc. As indicated earlier, cavitation is also capable of imparting chemical functional groups to graphene sheets while being produced via the cavitation-induced exfoliation and separation process. This unexpected feature enables concurrent production of graphene sheets and controllably varying the chemical and physical properties of graphene. Chemical functionalization could be used for engineering the properties of graphene towards specific applications.

A wide variety of chemical functional groups can be imparted to graphene sheets (e.g. biradical groups, such as dichlorocarbene and nitrene) while the graphene sheets are being produced. This process could provide facile, green, and cost-effective production of functionalized NGPs. To evaluate the technical feasibility of the single-step methodology, a series of functional bi-radical or azide compounds (f-azides) were used to react with concurrently produced single-layer and multi-layer NGPs. Each f-azide molecule utilized contains an azido group on one end and a functional group (e.g., —OH, —NH$_2$, —COOH, or —Br) on another end. These were used as examples only, not intended for limiting the scope of our invention, nevertheless. Once the azido group anchors on a primary surface of an NGP, a second functional group extends into the surrounding solvent to help solubilize the NGP. This second functional group is suitable for further chemical modification if so desired.

The azide compounds herein discussed may be selected from the group consisting of 2-Azidoethanol, 3-Azidopropan-1-amine, 4-(2-Azidoethoxy)-4-oxobutanoic acid, 2-Azidoethyl-2-bromo-2-methylpropanoate, chlorocarbonate, azidocarbonate, dichlorocarbene, carbene, aryne, nitrene, (R—)-oxycarbonyl nitrenes, and combinations thereof, where R=any one of the following groups:

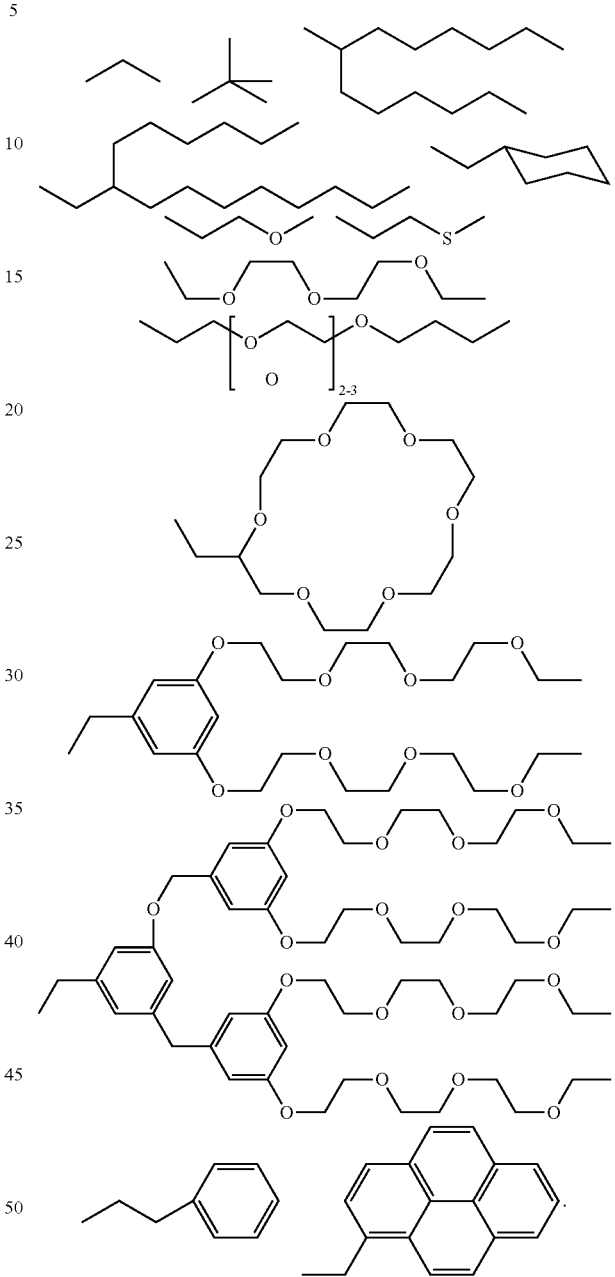

With functional groups being covalently anchored to the NGPs, the functionalized graphene sheets (f-NGPs) exhibit improved solubility/dispersibility in a solvent and enhanced interfacial adhesion between NGPs and a polymer matrix in a composite. Further, we have found it possible to directly graft polymers from the f-NGP surfaces with the functional groups acting as initiating sites.

Thus, another preferred embodiment of the present invention is a method of producing chemically functionalized and polymer-grafted graphene materials. This method includes mixing a graphitic material, an azide compound, and an organic solvent in a cavitation reactor and allowing concurrent production of graphene sheets and a chemical reaction between the graphene sheets and the azide compound to proceed at a temperature for a length of time sufficient to produce NGPs with a desired functional group attached thereto. This step is followed by a chain grafting or polymerizing step by which a polymer chain is attached to or reacted with the desired functional group.

In this cavitation-enabled process, the azide compound may be added to the liquid medium before the cavitation power is turned on. Alternatively, the azide compound may be added sequentially after the graphite material-liquid suspension is subjected to cavitation for some period of time. Both procedure sequences are very effective in generating functionalized NGPs.

Further alternatively, functionalized NGPs may be manufactured from intercalated or oxidized graphite. In one route, the process begins with preparation of oxidized graphite or graphite oxide powder. The oxidized graphite or graphite oxide is not subsequently subjected to exfoliation and separation treatments, as would be done in the production of graphite worms. Instead, the oxidized graphite powder and an azide compound are added to a solvent to produce a graphite oxide-azide suspension in a reactor. This suspension is then subjected to a cavitation treatment, which facilitates cocurrent exfoliation, separation, and functionalization of GO sheets to produce functionalized NGPs. In other words, the exfoliation and separation operations of the oxidized graphite are integrated with the chemical functionalization operation into one step, which is carried out inside the same hydrodynamic cavitation reactor.

In another route, the graphite material is intercalated, oxidized, or halogenated to produce graphite intercalation compound (GIC), graphite oxide, or halogenated graphite, etc. The GIC, graphite oxide, or halogenated graphite is then exposed to a thermal shock (e.g., at a temperature typically from 300° to 1,050° C. for 30-60 seconds) to produce exfoliated graphite (graphite worms). Without subjecting to a prior separation treatment (e.g., using an air jet mill, high-shear mixer, or ultrasonicator), the exfoliated graphite is mixed with chemical functional group-containing species (e.g. an azide compound) in a solvent contained in a cavitation reactor. The resulting suspension is then subjected to cavitation, which not only breaks up graphite worms to form separated NGPs, but also functionalize the NGPs substantially at the same time in the same reactor.

The invented cavitation-based, single-step production technology for preparing functional NGPs has several major advantages: (1) Azides (or bi-radical compounds) can be synthesized in large quantities under relatively mild conditions; (2) The process is environmentally friendly since the decomposed gas is nitrogen and the solvent can be recycled; (3) The functionalization process does not induce severe damage to NGPs; (4) Almost no other functional group except the desired one is anchored on the NGPs, making the f-NGPs structurally well-defined materials; (5) Various functional groups (for example, —OH, —NH$_2$, —COOH, —Br) can be introduced onto NGPs in merely one reaction; (6) The reaction can be easily performed under mild reaction conditions; and (7) The approach is applicable to functionalization of both pristine NGPs and oxidized NGPs (or GO).

The aforementioned processes are highly innovative and have not been taught implicitly or explicitly in the prior art. Hence, in summary, a preferred embodiment of the present invention is a combined production-functionalization process for manufacturing a chemically functionalized graphene material directly from a non-intercalated and non-oxidized graphite material (pristine graphite material). This process comprises (A) dispersing the pristine graphite material and a chemical functional group-containing species (e.g. an azide compound) in a liquid medium comprising a liquid (e.g. solvent) to form a suspension; and (B) subjecting the suspension to cavitation with a desired intensity for a length of time sufficient to produce graphene sheets and to enable a chemical reaction to occur between the graphene sheets and a chemical functional group to produce the functionalized graphene material.

Still another preferred embodiment of the present invention is a combined production-functionalization process for manufacturing a chemically functionalized graphene material directly from an intercalated, oxidized, or halogenated graphite material. This process comprises (A) producing exfoliated graphite from the intercalated, oxidized, or fluorinated graphite material; (B) dispersing the exfoliated graphite and a functional group-containing species in a liquid medium comprising a liquid (e.g. water or organic solvent) to form a suspension; and (C) subjecting the suspension to hydrodynamic cavitation of a desired intensity for a length of time sufficient to produce graphene sheets and to enable a chemical reaction to occur between the graphene sheets and the chemical functional group to produce the functionalized graphene material.

A further preferred embodiment of the present invention is a combined production-functionalization method and related process for manufacturing a chemically functionalized graphene material directly from an intercalated, oxidized, or halogenated (e.g., fluorinated) graphite material. The process or method comprises (A) dispersing said intercalated, oxidized, or fluorinated graphite material and a chemical functional group-containing species (e.g. an azide compound) in a liquid medium comprising a liquid to form a suspension; and (B) subjecting the suspension to cavitation with a desired intensity for a length of time sufficient to produce graphene sheets and to enable a chemical reaction to occur between the graphene sheets and the functional group to produce the functionalized graphene material.

In an embodiment, a combined production-functionalization method for manufacturing a chemically functionalized graphene material from a graphite material has been developed. This highly innovative method comprises: (A) Dispersing a graphite material and a bi-functional or multi-functional compound in a liquid medium to form a suspension; and (B) Subjecting the suspension to cavitation with a desired intensity or power level for a length of time sufficient to produce graphene sheets and to enable a chemical reaction to occur between the graphene sheets and the compound to produce the functionalized graphene material.

The bi-functional or multi-functional compounds have two, three, or four functional groups (e.g., diamine, tri-amine groups, etc. at their two, three or four ends, respectively). At least one of the functional groups is capable of reacting with an NGP at an edge or graphene plane. Azide compounds are among many available di-functional and multi-functional compounds suitable for use in this highly versatile process. It appears that high-power cavitation reactor is capable of activating the edges or graphene planes of NGPs and enabling many functionalization reactions to readily initiate and proceed. The graphite material may be selected from a wide range of graphitic materials, including natural graphite, artificial graphite, highly oriented pyrolytic graphite, carbon fiber, graphite fiber, carbon nano-fiber, graphitic nano-fiber, meso-carbon micro-bead, graphitized coke, pre-intercalated versions thereof, pre-oxidized versions thereof, pre-fluorinated versions thereof, chemically modified versions thereof, and combinations thereof. Oxidation, fluorination, and other chemical modifications (e.g., bromination) of graphite are well-known in the art. Other halogenated graphite materials, such as chlorinated graphite ($C_8Cl$) and brominated graphite ($C_8Br$), can be obtained by making a graphite material to react with a halogen or halogen compound at a temperature greater than room temperature. The presently invented process is applicable to pristine versions and various chemically modified versions of the above-listed graphitic materials.

The chemically functionalized graphene materials produced with this process typically comprise a significant portion of single-layer graphene. The chemical reaction can be controlled to occur only to an edge or edges of the graphene sheets or, alternatively, to an edge and at least one primary surface, graphene plane, of the graphene sheets.

The following examples serve to provide the best modes of practice for the present invention and should not be construed as limiting the scope of the invention:

Example 1

Production of Graphene Sheets (NGPs) from Pristine Natural Graphite

Five grams of natural graphite flakes, ground to approximately 20 μm or less in sizes, were dispersed in 1,000 mL of deionized water (containing 0.1% by weight of a dispersing agent or surfactant, Zonyl® FSO from DuPont) to obtain a suspension. A laboratory-scale hydrodynamic cavitation reactor was operated to induce cavitation in water for 5 minutes to 1 hour (Sample 1C-s, 1 hour). For comparison purpose, an ultrasonic wave generator with an energy level of 85 W (Branson S450 Ultrasonicator) was operated for exfoliation, separation, and size reduction of graphene sheets for a period of 1 hour (Sample 1U-s).

Other preferred surfactants that can be used in a cavitation reaction include: anionic surfactants, nonionic surfactants, cationic surfactants, amphoteric surfactants, silicone surfactants, fluoro-surfactants, polymeric surfactants, sodium hexametaphosphate, sodium lignosulphonate, poly(sodium 4-styrene sulfonate), sodium dodecylsulfate, sodium sulfate, sodium phosphate, and sodium sulfonate. These surfactants when dispersed in a liquid medium (e.g. water) were found to readily wet graphene or graphite surfaces.

Example 2

Production of NGPs from Natural Graphite Flakes (No Surfactant)

Five grams of natural graphite flakes (same as in Example 1), ground to approximately 20 μm or less in sizes, were dispersed in 1,000 mL of deionized water to obtain a suspension. The same cavitation reactor was operated to induce cavitation in water for 5 minutes to 1 hour (Sample 2C-ns, 1 hour). The same ultrasonic wave generator at an energy level of 85 W (Branson S450 Ultrasonicator) was used for exfoliation, separation, and size reduction of graphene sheets for a period of 1 hour (Sample 2U-ns).

Example 3

Exfoliation and Separation of Graphite Oxide to Produce Graphene Oxide Sheets Graphite oxide was prepared by oxidation of graphite flakes with sulfuric acid, nitrate, and potassium permanganate according to the method of Hummers [U.S. Pat. No. 2,798,878, Jul. 9, 1957] for 5 hours (Sample 3A) and 24 hours (Sample 3B). Upon completion of the reaction, the mixture for each sample was poured into deionized water and filtered. The graphite oxide was repeatedly washed in a 5% solution of HCl to remove most of the sulphate ions. The sample was then washed repeatedly with deionized water until the pH of the filtrate was neutral. The slurry was spray-dried and stored in a vacuum oven at 60° C. for 24 hours. The interlayer spacing of the resulting laminar graphite oxide was determined by the Debey-Scherrer X-ray technique to be approximately 0.73 nm (7.3 Å). The two samples were then subjected to various combinations of thermal exfoliation, hydrodynamic cavitation, and ultrasonication treatments, as summarized below:

Sample 3A-Ex: graphite oxide (GIC) was subjected to thermal exfoliation at 1,050° C. for 1 minute to produce exfoliated graphite or graphite worms.

Sample 3A-C: graphite oxide (GIC) was subjected to hydrodynamic cavitation for 10 minutes to produce graphene oxide sheets (oxidized version of NGPs, or GO).

Sample 3A-U: graphite oxide (GIC) was subjected to ultrasonication for 10 minutes to produce graphene oxide sheets.

Sample 3A-Ex-C: graphite worms (portion of Sample 3A-Ex) were subjected to hydrodynamic cavitation for 5 minutes to produce graphene oxide sheets by breaking up graphite worm structures and separating individual graphene sheets.

Sample 3A-Ex-U: graphite worms (portion of Sample 3A-Ex) were subjected to ultrasonication for 5 minutes to produce graphene oxide sheets by breaking up graphite worm structures and separating individual graphene sheets.

Sample 3B-C: graphite oxide (Sample 3B) was subjected to hydrodynamic cavitation for 5 minutes to produce graphene oxide sheets.

Sample 3B-U: graphite oxide (Sample 3B) was subjected to ultrasonication for 5 minutes to produce graphene oxide sheets.

The dimensions and electrical conductivity values of the exfoliated and separated graphene oxide sheets or NGPs of Samples 1-3 are summarized in Table 1. The electrical conductivity was measured on NGP paper prepared by vacuum-assisted filtration, followed by compression.

TABLE 1

Dimensions and electrical conductivity of NGPs prepared under different conditions.

| Sample | Average platelet length (μm) | Average NGP thickness (nm) | In-plane electrical conductivity of NGP paper (S/cm) |
|---|---|---|---|
| Sample 1C-s | 4.8 | 1.2 | 3,845 |
| Sample 1U-s | 3.2 | 4.3 | 3,305 |
| Sample 2C-ns | 3.5 | 3.5 | 3,500 |
| Sample 2U-ns | 1.6 | 28.6 | 1,800 |
| Sample 3A-Ex | Graphite worms | Graphite worms | 1,250 |

TABLE 1-continued

Dimensions and electrical conductivity of NGPs prepared under different conditions.

| Sample | Average platelet length (μm) | Average NGP thickness (nm) | In-plane electrical conductivity of NGP paper (S/cm) |
|---|---|---|---|
| Sample 3A-C | 3.3 | 1.4 (>80% single-layer) | 1,325 |
| Sample 3A-U | 2.5 | 2.1 (45% single-layer) | 1,290 |
| Sample 3A-Ex-C | 2.2 | 1.3 (>85% single-layer) | 1,525 |
| Sample 3A-Ex-U | 2.0 | 2.5 (25% single-layer) | 1,310 |
| Sample 3B-C | 1.2 | 1.0 (100% single-layer GO) | 75 |
| Sample 3B-U | 0.9 | 1.0 (100% single-layer GO) | 44 |

It is of significance to make the following observations:
(a) The presently invented approach of utilizing a dispersing agent or surfactant in a liquid medium enables the hydrodynamic cavitation reactor to produce NGPs that are much thinner (e.g., 1.2 nm in Sample 1C-s) as compared to a suspension without a surfactant (e.g., 3.5 nm in Sample 2C-ns).
(b) Without a high-temperature exposure (hence, relatively oxidation-free), this new approach also leads to NGPs with a much higher electrical conductivity; e.g., 3,500-3,845 S/cm as opposed to approximately 1,500 S/cm or lower commonly reported for commercially available flexible graphite sheet (e.g. from Sample 3A-Ex).
(c) A comparison between Sample 1C-s and Sample 1U-s, between Sample 2C-ns and Sample 2U-ns, between Sample 3A-C and Sample 3A-U, between Sample 3A-Ex-C and Sample 3A-Ex-U, and between Sample 3B-C and Sample 3B-U indicates that the hydrodynamic cavitation method is more effective than ultrasonication method in terms of producing longer/wider graphene sheets that are thinner (fewer graphene planes per sheet).

Example 4

NGP Nanocomposites

Approximately 2 grams of NGPs prepared by spray-drying a portion of the sample prepared in Example 1 was added to 100 mL of water and a 0.2% by weight of a surfactant, sodium dodecylsulfate (SDS), to form a slurry, which was then subjected to hydrodynamic cavitation at approximately 20° C. for five minutes. A stable dispersion (suspension) of well-dispersed NGPs was obtained. A water-soluble polymer, polyethylene glycol (PEG, 1% by weight), was then added to the suspension. Water was later vaporized, resulting in a nanocomposite containing NGPs dispersed in a polymer matrix. In this process, the polymer was introduced after graphene sheets were produced.

In an alternative route, the polymer was dissolved in water along with SDS surfactant prior to the production of graphene sheets. Powder of natural graphite was dispersed in the PEG/SDS/water medium to form a suspension, which was introduced into a hydrodynamic cavitation reactor. Surprisingly, the presence of polymer chains in a cavitating liquid did not have any negative effect on the production of graphene sheets. Graphene production, graphene dispersion, and polymer mixing were accomplished in a single step to form a precursor composite suspension. This precursor composite suspension was then cast on a glass surface to form a composite layer upon removal of water and surfactant at 85° C.

Example 5

NGPs from Short Carbon Fiber Segments

The procedure was similar to that used in Example 1, but the starting material was graphite fibers chopped into segments with 0.2 mm or smaller in length prior to dispersion in water. Chopped graphite fibers were then washed and treated in a sulfuric acid bath for 30 minutes to change the surface characteristics of fibers for improved dispersion in water and wettability by water and surfactant. The diameter of carbon fibers was approximately 12 μm. After hydrodynamic cavitation for 3 hour, the graphene platelets exhibit an average thickness of 4.8 nm.

Example 6

NGPs from Carbon Nano-Fibers (CNFs)

A powder sample of graphitic nano-fibers was prepared by introducing an ethylene gas through a quartz tube pre-set at a temperature of approximately 800EC. Also contained in the tube was a small amount of nano-scaled Cu—Ni powder supported on a crucible to serve as a catalyst, which promoted the decomposition of the hydrocarbon gas and growth of CNFs. Approximately 2.5 grams of CNFs (diameter of 10 to 80 nm) were dispersed in water (as in Sample 1). The sample was then subjected to hydrodynamic cavitation at 20° C. for 15 minutes to effect exfoliation and separation. Fine NGPs with an average thickness of 1.5 nm were obtained.

Example 7

Graphene Oxide Nano Platelets, their Nanocomposites, and their Reduced Versions

The GO sheets (portion of Sample 3B-C) were well-dispersed in water, forming a stable water dispersion (suspension). Upon removal of water, the GO sheets settled to form an ultra-thin nano-carbon film (a mat or paper). A small amount of water-soluble polymer (e.g., poly vinyl alcohol) was added to the GO sheet-water suspension with the polymer dissolved in water. The resulting nano platelet suspension with polymer-water solution as the dispersing medium was also very stable. Upon removal of water, polymer was precipitated out to form a thin coating on nano platelets. The resulting structure is a GO-reinforced polymer nanocomposite.

A small amount of the GO-water suspension was reduced with hydrazine hydrate at 100° C. for 24 hours. As the reduction process progressed, the brown-colored suspension of graphene oxides turned black, which appeared to become essentially reduced graphene oxide (RGO) sheets.

Another attempt was made to carry out the reduction of the GO sheets prepared via the presently invented method. In this case, hydrazine hydrate reduction was conducted in the presence of poly(sodium 4-styrene sulfonate) (PSS with Mw=70,000 g/mole). A stable dispersion was obtained, which led to PSS-coated NGPs upon removal of water. This is another way of producing graphene-based nanocomposites.

Example 8

Production and Oxidation of NGPs from Artificial Graphite

Twenty (20) mg of meso-phase pitch-derived graphite of approximately 20 μm in diameter used in each of the following samples:

Sample 8A: graphite was added to a mixture of 20 mL of formic acid and 1 mL of hydrogen peroxide and the resulting suspension was subjected to hydrodynamic cavitation for 5 minutes. Electron microscopic examinations of selected samples indicate that the majority of the resulting NGPs (GO sheets) contain between single graphene sheet and 10-layer graphene sheets.

Sample 8B: graphite was immersed in a mixture of 2 mL of formic acid and 1 mL of hydrogen peroxide at 45° C. for 24 hours. Following the chemical oxidation/intercalation treatment, the resulting intercalated graphite were washed with water and dried. The resulting product is a formic acid-intercalated graphite compound. The dried GIC was then placed in a cavitation reactor for 5 minutes. The thickness of the resulting platelets ranges from 1 graphene sheet to approximately 5-layer graphene sheets based on SEM and TEM observations.

Additional GO samples were prepared by combined production and oxidation of graphene sheets from graphite particles that have never been previously exposed to chemical oxidation or intercalation. The oxidizing agents evaluated were nitric acid, sodium nitrate, and potassium permanganate, which were found to be effective as a concurrent oxidizing agent during hydrodynamic cavitation-induced production of graphene sheets. This example has demonstrated the surprising effectiveness of hydrodynamic cavitation. Both formic acid and hydrogen peroxide are environmentally benign.

Figure 4A:
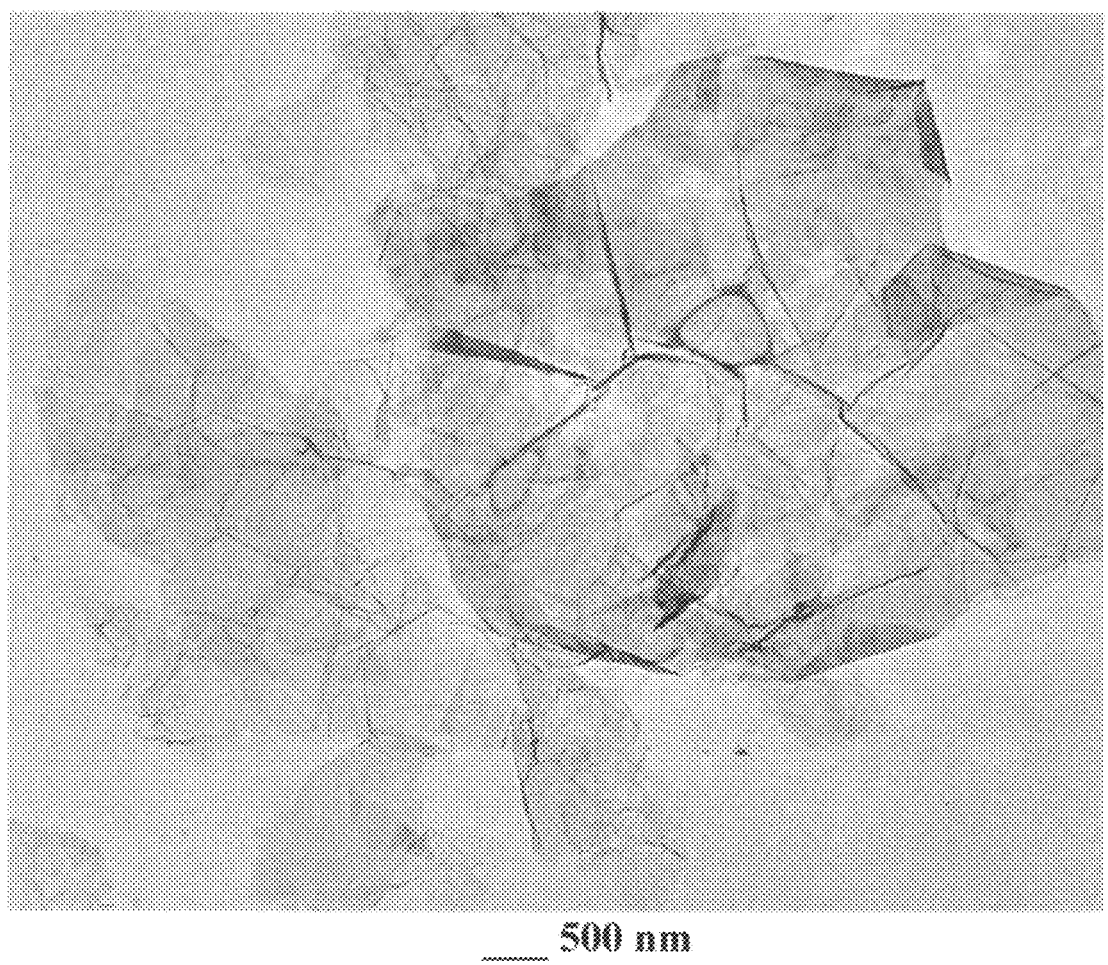
FIG. 4 Transmission electron micrographs of (A) NGPs produced by the hydrodynamic cavitation process (wider and longer graphene sheets) and (B) NGPs produced by conventional Hummer's route (much smaller graphene sheets, but comparable thickness)
Figure 4B:
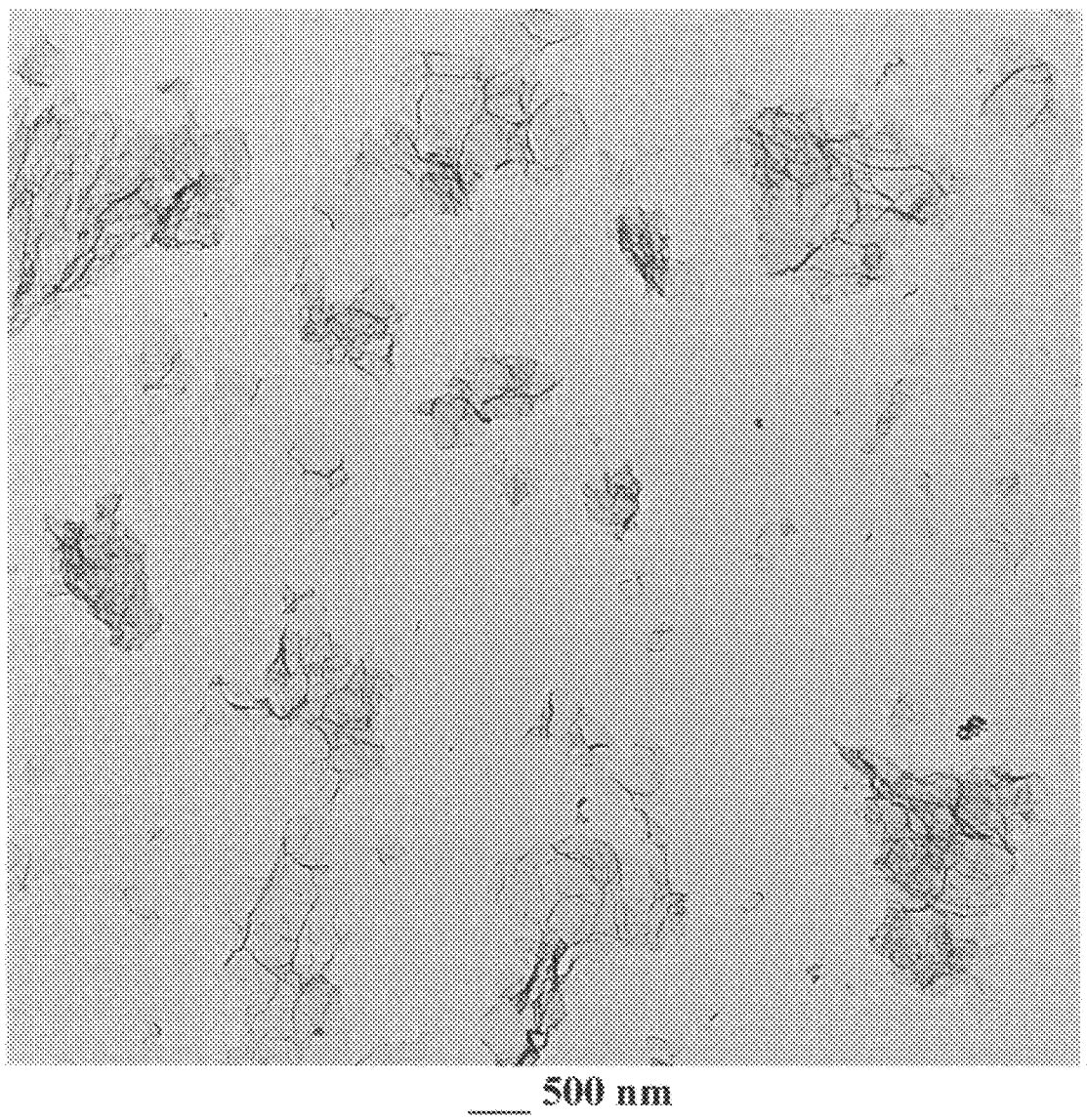

These results, along with the data summarized in Table 1 above, have clearly demonstrated the superiority of the presently invented hydrodynamic cavitation method of producing graphene materials over conventional chemical oxidation/intercalation method. Both methods are capable of producing single-layer graphene, but our method produces graphene sheets that are wider, longer (FIG. 4A), and much more electrically conducting. The conventional Hummer's method and all other chemical oxidation/intercalation method necessarily involve highly oxidizing the graphitic material, creating damage (defects) to the resulting graphene sheets that could never be repaired or recovered (smaller lateral dimensions, FIG. 4B). Even after heavy chemical reduction with hydrazene, the graphene material (a reduced graphene oxide) still exhibits an electrical conductivity one order of magnitude lower than that of the more pristine graphene produced by the hydrodynamic cavitation method.

Another highly significant and most surprising result is the observation that diluted acid/oxidizer works equally well with concentrated acid/oxidizer. These unexpected discoveries have very significant impacts in terms of environmental protection.

Example 9

Combined Production and Chemical Functionalization of Graphene Sheets

The graphene sheets produced by hydrodynamic cavitation can be concurrently functionalized by adding a reactant that contains a desired functional group to the graphite-liquid suspension in a hydrodynamic cavitation reactor. The functional group may be selected from, as examples, alkyl or aryl silane, alkyl or aralkyl group, hydroxyl group, amine group, fluorocarbon, or a combination thereof.

(a) Graphite+$CH_2$=CHCOX (at 95° C.) in a liquid→Graphene-R'COH (where X=—OH, —Cl, —$NH_2$, or —H); e.g., graphite+$CH_2$=CHCOOH+water→G-R'CO—OH (where G=graphene) dispersed in water;

(b) Graphite+Maleic anhydride+water→G-R'$(COOH)_2$ in water;

(c) Graphite+Cyonogen+AIN (acetone nitrile)→G-CN in AIN;

(d) Graphite+$CH_2$=CH—$CH_2$X+liquid (e.g. water or organic solvent)→G-R'$CH_2$X (where X=—OH, -halogen, or —$NH_2$) in liquid;

(e) Graphite+$H_2O_2$ in water→G=O (Quinoidal), a graphene oxide;

(f) Graphite+$CH_2$=CHCHO→G-R'CHO (Aldehydic);

(g) Graphite+$CH_2$=CH—CN+solvent→G-R'CN in solvent.

In the above-listed reactions, R' is a hydrocarbon radical (alkyl, cycloalkyl, etc). Chemical functionalization treatments can be used to vary the solubility or dispersibility of NGPs without significantly compromising electrical conductivity. The functional groups attached to graphene sheets can be selected to improve the dispersibility in or chemical bond with a resin to form a resin composite with improved mechanical properties.

Example 10

Concurrent Production and Functionalization of GO Sheets

The presence of a functional group-containing species in the suspension of graphite oxide particles in water, upon hydrodynamic cavitation, can lead to the production of GO sheets and the attachment of the functional groups on a surface or at an edge of a graphene plane, including carboxylic acid and hydroxyl groups. A large number of derivatives can then be prepared from carboxylic acid alone. For instance, alcohols or amines can be easily linked to acid to provide stable esters or amides. If the alcohol or amine is part of a di- or poly-functional molecule, then linkage through the O— or NH— leaves the other functional group(s) as pendant group(s). For instance, we can have R—OH or R—$NH_2$, where R=alkyl, aralkyl, aryl, fluoroethanol, polymer, and $SiR'_3$. Examples include Cl—$SiR'_3$, HO—R—OH (R=alkyl, aralkyl, or $CH_2O$—), $H_2N$—R—$N_2H$ (R=alkyl, aralkyl), X—R—Y (R=alkyl, etc.; X=OH or $NH_2$; Y=SH, CN, C=O, CHO, alkene, alkyne, aromatic, or heterocycles).

As an example, GO was treated to follow the following reactions: R—COOH+Im-CO-Im→R—CO-Im+Him+$CO_2$ (Im=imidazolide) and Him=imidazole), which was followed by R—CO-Im+R'OH (in NaOEt)→R—CO—OR'+HIm, and, separately for another specimen, by R—CO-Im+R'$NH_2$→R—CO—NHR'+Him.

Example 11

Preparation of bi-radical or azide-derived functional groups (e.g. 2-Azidoethanol, 3-Azidopropan-1-amine, 4-(2-Azidoethoxy)-4-oxobutanoic Acid, and 2-Azidoethyl-2-bromo-2-methylpropanoate)

In a typical procedure, a solution of sodium azide (195 g, 3.0 mol) in deionized water (780 mL) and 2-chloroethanol (120.8 g, 1.5 mol) was to a 2000 mL three-neck round-bottom flask equipped with a condenser. The flask was immersed in an oil bath at 70° C. and stirring was maintained for 96 h. After cooling to room temperature, the reaction mixture was extracted with diethyl ether (5×100 mL). The extracts were dried over anhydrous MgSO$_4$ overnight, filtered, concentrated on a rotary evaporator, and distilled under reduced pressure to produce an oil-like, colorless substance. The yield was 214.4 g or 82%.

A solution of sodium azide (195 g, 3.0 mol) in deionized water (800 mL) was added into a three-neck round-bottom flask equipped with a condenser. Then 3-chloropropylamine hydrochloride (195 g, 1.5 mol) dissolved in 300 mL of deionized water was added. After continued stirring at 75-78° C. for 96 h, the white precipitate (NaCl) was removed as a byproduct from the reaction mixture by filtration. The yellow filtrate was basified with aqueous NaOH to pH 10-11 and further extracted with diethyl ether (5×200 mL). The organic fraction was dried over anhydrous MgSO$_4$ overnight, filtered, concentrated on a rotary evaporator, and distilled under reduced pressure to produce a colorless oil. The yield was: 108.4 g, 72%. 1H NMR (CDCl$_3$, δ, ppm): 3.35 (t, 2H, CH$_2$N$_3$), 2.78 (t, 2H, NH$_2$CH$_2$), 1.71 (p, 2H, CH$_2$CH$_2$CH$_2$), 1.27 (s, 2H, NH$_2$).

Succinic anhydride (23.0 g, 0.230 mol) was added into a three-neck round-bottom flask equipped with a condenser and a dropping funnel. Under nitrogen atmosphere and magnetic stirring, freshly distilled methylene chloride (150 mL), DMAP (2.3 g, 19 mmol) and freshly distilled Et3N (46.46 g, 0.460 mol) was sequentially added. After the flask was immersed into an ice-water bath, 2-azidoethanol (20.0 g, 0.230 mol) was added dropwise into the previous solution. The solution was later heated at 40° C. for 48 h, and the reaction mixture was washed successively with 1 M HCl solution (5×100 mL) and deionized water (2×100 mL). The organic phase was dried over anhydrous MgSO$_4$ overnight. After filtering and removal of methylene chloride under reduced pressure, the final product was obtained as a yellow viscous liquid. The yield was: 38.4 g, 90%. 1H NMR (CDCl$_3$, δ, ppm): 4.20 (t, 2H, N$_3$CH$_2$CH$_2$), 3.42 (t, 2H, N$_3$CH$_2$), and 2.61 (m, 4H, CH$_2$CH$_2$COOH).

2-Azidoethanol (17.40 g, 0.2 mol), freshly distilled methylene chloride (150 mL), and Et3N (21.21 g, 0.21 mol) were added into a three-neck round-bottom flask equipped with a condenser and a dropping funnel. Under nitrogen atmosphere and magnetic stirring, freshly distilled anhydrous methylene chloride (150 mL), DMAP (1.7 g, 14 mmol), and freshly distilled anhydrous Et3N (46.5 g, 0.46 mol) were sequentially added. After the flask was immersed into an ice-water bath, 2-bromoisobutyryl bromide (48.28 g, 0.21 mol) was added dropwise into the previous solution. Twenty-four hours later, the reaction mixture was washed successively with 1 M HCl (3×200 mL) solution and deionized water (1×200 mL). The organic phase was dried over anhydrous MgSO$_4$ overnight. After filter and removal of methylene chloride on a rotary evaporator, the obtained residues were distilled under reduced pressure to give a colorless viscous liquid. The yield was: 33.4 g, 70%. 1H NMR (CDCl$_3$, δ, ppm): 4.24 (t, 2H, N$_3$CH$_2$CH$_2$), 3.52 (t, 2H, N$_3$CH$_2$), 1.96 (s, 6H, (CH$_3$)2Br).

Example 12

Production of NGP-OH, NGP-NH$_2$, NGP-COOH, and NGP-Br

In a typical experiment (feed ratio, $R_{feed}$=20/1 (w/w)), pristine graphite (1.00 g), N-methyl-2-pyrrolidinone (NMP, 80 mL), and 2-azidoethanol (20.0 g, 0.23 mol) were introduced into a hydrodynamic cavitation reactor. The reaction mixture was then heated and maintained around 100° C. for 1 h. After cooling down to room temperature, the product was isolated by precipitation into acetone. The resulting precipitates were re-dispersed in acetone with the aid of an ultrasonic bath and then collected by centrifugation. This centrifugation was repeated until the upper layer was nearly colorless. The separated solid was sequentially re-dispersed in water and purified by centrifugation. The supernatant was decanted and the black solid was dried under vacuum at 60° C. overnight to give 1.04 g of NGP-OH. Thus, this is a weight-increase process, and the mass loss of neat graphite during the preparation methods is less than 10%. One additional batch of 5-10 g of non-pristine NGPs (GO) was subjected to cavitation to produce, dispersed functionalized NGPs.

The same procedure was also used to prepare NGP-NH$_2$, NGP-COOH, and NGP-Br, but 2-azidoethanol was substituted by 3-azidopropan-1-amine, 4-(2-azidoethoxy)-4-oxobutanoic acid, and 2-azidoethyl 2-bromo-2-methylpropanoate, respectively.

Example 13

Synthesis of NGP-g-PCL by Concurrent Graphene Production and Ring-Opening Polymerization (ROP)

Into a 50 mL of the reaction mass intended for preparing NGP-OH ($R_{feed}$=20/1, 50 mg) was charged with high-purity ε-Caprolactone (6.0 g, 53 mmol) and stannous octoate (2 mg). The reaction was allowed to proceed at 100° C. for 1 h and then for 1 h at 120° C. The product was filtered and washed thoroughly with excess chloroform several times. The final product was dried under vacuum overnight to give 53 mg of NGP-g-PCL, graphene sheets grafted to polycaprolactone. This example demonstrates that hydrodynamic cavitation can promote or facilitate polymerization.

Example 14

NGP-g-PGMA by Concurrent Graphene Production and Cationic ROP

Into a 20 mL of the reaction mass intended for preparing NGP-OH ($R_{feed}$=20/1, 20 mg), dried CH$_2$Cl$_2$ (15 mL) and GMA (4.0 g, 28 mmol) were added under nitrogen. The cavitation reactor was then turned on for 1 min and then BF$_3$.OEt$_2$ (0.1 mL) was injected into the reaction mixture. After 2 h, the cationic polymerization was ended by adding a small amount of methanol. The resulting product was washed with methanol and separated by centrifuging. The final product was dried under vacuum overnight to give 17 mg of NGP-g-PGMA.

Example 15

Production and Functionalization (Amidation) of Graphene Sheets

Natural graphite (18 mg) and 1 mg of diethylenetriamine (HN(CH$_2$CH$_2$NH$_2$)$_2$) were dispersed and dissolved, respectively, in water to form a suspension. The suspension was introduced into a hydrodynamic reactor and the reaction was allowed to proceed at room temperature for 2 h. The product was isolated by centrifugation and rinsed in turn with 1 M HCl and deionized water. The black solid was collected and dried overnight under vacuum to give 17 mg of amine-functionalized NGP.

Example 16

Characterization of Materials Synthesized

A combination of the following techniques, when deemed necessary, was used to characterize the functional groups attached to NGPs for functionalized versions of both pristine graphene and graphene oxide:

(1) Thermogravimetric analysis (TGA) was used to determine the level of surface functionalization. Since most functional groups were labile or decompose upon heating, and the NGPs are stable up to 1200° C. under argon (Ar) atmosphere, the weight loss at 800° C. under Ar was used to determine functionalization ratio.
(2) X-ray photoelectron spectroscopy (XPS) was used to confirm the presence of different elements in functionalized NGPs. De-convolution of XPS signals was useful for studying fine structures on NGPs.
(3) Raman spectroscopy: The tangential G mode (ca. 1550-1600 $cm^{-1}$) was characteristic of $sp^2$ carbons on the hexagonal graphene network. The D-band, so-called disorder mode (found at ca. 1295 $cm^{-1}$), appears due to disruption of the hexagonal $sp^2$ network of NGPs. The D-band was be used to characterize functionalized NGPs and ensure that functionalization is covalent and occurs on the primary surfaces of a graphene sheet.
(4) Infrared (IR) spectroscopy was useful in characterizing functional groups bound to graphene surfaces. A variety of organic functional groups on graphene surfaces, such as COOH(R), —$CH_2$, —$CH_3$, —$NH_2$, and —OH, were identified using FTIR.
(5) UV/visible spectroscopy was used to provide information about the electronic states of NGPs, and hence functionalization. The absorption spectra showed bands near 1400 nm and 1800 nm for pristine NGPs. A loss or shift of such structure was be observed after chemical alteration of NGP surfaces.
(6) Solution $^1H$ NMR was of adequate sensitivity for characterizing NGPs functionalized by carbenes and nitrenes because of the high solubility of derivatized NGPs. Solid state $^{13}C$ NMR was employed to characterize several functionalized NGPs and show successful observation of organic functional groups, such as carboxylic and alkyl groups on graphene surfaces and edges.
(7) Atomic force microscopy (AFM) and transmission electron microscopy (TEM were used to characterize both un-treated and functionalized NGPs. The height profile on AFM was used to show presence of functional groups on a NGP surface. Measurements of heights along an individual graphene plane could be correlated with the substituent group, i.e., the larger an alkyl chain of a surface substituent, the greater the height measured.

The invention claimed is:

1. A method of producing a graphene material directly from a starting graphitic material, said method comprising: (a) dispersing said starting graphitic material and an oxidizing agent or a chemical functionalization agent in a liquid medium to form a graphite suspension, wherein said starting graphitic material is a pristine graphitic material that has never been previously intercalated or oxidized ; and (b) introducing said graphite suspension into a hydrodynamic cavitation reactor that exfoliates and separates graphene planes from said starting graphitic material and generates and collapses cavitation or bubbles in said liquid medium to produce said graphene material and to oxidize or chemically functionalize said graphene material to produce a graphene oxide or a chemically functionalized graphene material dispersed in said liquid medium.

2. The method of claim 1, wherein said hydrodynamic cavitation reactor operates by passing a liquid through a constricted channel at a specific velocity to produce cavitation or micro-bubbles.

3. The method of claim 1, wherein said liquid medium contains water, an alcohol, or a water-alcohol mixture.

4. The method of claim 1, wherein said liquid medium contains a surfactant.

5. The method of claim 4, wherein said surfactant is selected from the group consisting of anionic surfactants, nonionic surfactants, cationic surfactants, amphoteric surfactants, silicone surfactants, fluoro-surfactants, polymeric surfactants, sodium hexametaphosphate, sodium lignosulphonate, poly (sodium 4-styrene sulfonate), sodium dodecylsulfate, sodium sulfate, sodium phosphate, sodium sulfonate, and combinations thereof.

6. The method of claim 1, wherein said liquid medium contains an organic solvent.

7. The method of claim 1, wherein said liquid medium contains an organic solvent selected from N-methylpyrrolidone (NMP), N,N-Dimethylacetamide (DMA), γ-butyrolactone (GBL), 1,3-dimethyl-2-imidazolidinone (DMEU), or a combination thereof.

8. The method of claim 1, wherein said liquid medium contains an organic solvent having a surface free energy that enables wetting of said liquid medium on a graphene plane of said starting graphitic material.

9. The method of claim 1 wherein said hydrodynamic cavitation reactor is operated at a temperature lower than 100° C.

10. The method of claim 1 wherein said starting graphitic material comprises natural graphite, synthetic graphite, highly oriented pyrolytic graphite, meso-carbon micro-bead, coke, graphitized meso-phase carbon, graphitized soft carbon, carbon or graphite fiber, carbon or graphitic nano-fiber, exfoliated graphite, expanded graphite, or a combination thereof.

11. The method of claim 1, wherein said liquid medium contains an ionic liquid which is an ionic salt having a melting temperature lower than 100° C.

12. The method of claim 1, wherein said liquid medium contains an acid.

13. The method of claim 1, wherein said liquid medium contains a weak acid selected from formic acid, acetic acid, nitric acid, maleic acid, or carboxylic acid.

14. The method of claim 1 wherein said graphene contains single-layer graphene sheets.

15. The method of claim 1 wherein said graphene contains at least 80% single-layer graphene sheets.

16. The method of claim 1, further comprising a step of converting said graphene material dispersed in said liquid medium into a paper, mat, or powder form.

17. The method of claim 1, further comprising a step of converting said graphene oxide or chemically functionalized graphene material dispersed in said liquid medium into a powder, paper, or mat form.

18. The method of claim 1, wherein said liquid medium further contains therein a monomer, oligomer, or polymer and said hydrodynamic cavitation reactor generates and collapses cavitation or bubbles in said liquid medium to produce said graphene material, disperse said graphene material in said liquid medium, and disperse or dissolve said monomer, oligomer, or polymer in said liquid medium to form a precursor composite suspension.

19. The method of claim 18, further comprising a step of converting said precursor composite suspension into a graphene-polymer nanocomposite.

20. The method of claim 1, wherein said liquid medium further contains therein a monomer, oligomer, or polymer, and said cavitation reactor generates and collapses cavitation or bubbles in said liquid medium to produce said graphene material, and to disperse said monomer, oligomer, or polymer in said liquid medium to produce a precursor composite suspension.

21. The method of claim 20, further comprising a step of converting said precursor composite suspension into a graphene-polymer nanocomposite.

22. The method of claim 1, wherein said liquid medium is a mixture containing an acid and an oxidizing agent.

23. The method of claim 1 wherein said liquid medium contains a carboxylic acid selected from the group consisting of aromatic carboxylic acid, aliphatic or cycloaliphatic carboxylic acid, straight chain or branched chain carboxylic acid, saturated and unsaturated monocarboxylic acids, dicarboxylic acids and polycarboxylic acids that have 1-10 carbon atoms, alkyl esters thereof, and combinations thereof.

24. The method of claim 23 wherein said carboxylic acid is selected from the group consisting of saturated aliphatic carboxylic acids of the formula $H(CH_2)_nCOOH$, wherein n is a number of from 0 to 5, including formic, acetic, propionic, butyric, pentanoic, and hexanoic acids, anhydrides thereof, reactive carboxylic acid derivatives thereof, and combinations thereof.

25. A method of producing a graphene material directly from a starting graphitic material, said method comprising: (a) dispersing said starting graphitic material in a liquid medium to form a graphite suspension; and (b) introducing said graphite suspension into a hydrodynamic cavitation reactor that exfoliates and separates graphene planes from said starting graphitic material to produce said graphene material dispersed in said liquid medium, wherein said graphite suspension further contains a monomer which is polymerized in said hydrodynamic reactor.

26. The method of claim 25, wherein said hydrodynamic cavitation reactor generates and collapses cavitation or bubbles in said liquid medium and said method further comprises a step of recovering said graphene material in a powder form from said liquid medium.

27. The method of claim 25, wherein said graphene material is pristine graphene.

28. The method of claim 25, wherein said hydrodynamic cavitation reactor includes a housing defining a cylindrical chamber, a cylindrical rotor rotatably mounted in the chamber, bores in a peripheral surface of the rotor, and a cavitation zone defined between the peripheral surface of the rotor and an interior wall of the chamber, and the step of introducing said graphite suspension comprises passing the graphite suspension through the cavitation zone as the rotor rotates.

29. The method of claim 25, wherein said starting graphitic material is an intercalated, oxidized, halogenated, nitrogenated, hydrogenated, or exfoliated form of a graphitic material selected from natural graphite, synthetic graphite, highly oriented pyrolytic graphite, meso-carbon micro-bead, coke, graphitized meso-phase carbon, graphitized soft carbon, carbon or graphite fiber, carbon or graphitic nano-fiber, or a combination thereof.

30. The method of claim 29, further comprising a step of converting said graphene material and a polymer dispersed in said liquid medium into a powder, paper, or mat form.

31. The method of claim 29, wherein said liquid medium further contains therein a chemical functionalization agent and said cavitation reactor generates and collapses cavitation or bubbles in said liquid medium to produce said graphene material and to chemically functionalize said graphene material to produce a chemically functionalized graphene material dispersed in said liquid medium.

32. The method of claim 31, further comprising a step of converting said chemically functionalized graphene material and a polymer dispersed in said liquid medium into a powder, paper, or mat form.

33. The method of claim 29, wherein said liquid medium further contains therein a monomer, oligomer, or polymer and said hydrodynamic cavitation reactor generates and collapses cavitation or bubbles in said liquid medium to produce said graphene material, disperse said graphene material in said liquid medium, and disperse or dissolve said monomer, oligomer, or polymer in said liquid medium to form a precursor composite suspension.

34. The method of claim 33, further comprising a step of converting said precursor composite suspension into a solid graphene-polymer nanocomposite.

35. The method of claim 25, wherein said starting graphitic material contains exfoliated graphite or expanded graphite, said liquid medium further contains therein an oxidizing agent, and said hydrodynamic cavitation reactor is operated to produce and oxidize said graphene material to produce a graphene oxide material dispersed in said liquid medium.

* * * * *